(12) United States Patent
Liggett et al.

(10) Patent No.: US 12,024,502 B2
(45) Date of Patent: Jul. 2, 2024

(54) BIASED ADRENERGIC AGONISTS

(71) Applicants: University of South Florida, Tampa, FL (US); The Florida International University Board of Trustees, Miami, FL (US)

(72) Inventors: Stephen Bryant Liggett, Treasure Island, FL (US); Donghwa Kim, Tampa, FL (US); Marcello Giulianotti, Vero Beach, FL (US)

(73) Assignees: University of South Florida, Tampa, FL (US); The Florida International University Board of Trustees, Miami, FL (US)

( * ) Notice: Subject to any disclaimer, the term of this patent is extended or adjusted under 35 U.S.C. 154(b) by 0 days.

(21) Appl. No.: 17/902,085

(22) Filed: Sep. 2, 2022

(65) Prior Publication Data

US 2023/0099379 A1    Mar. 30, 2023

Related U.S. Application Data

(60) Provisional application No. 63/240,120, filed on Sep. 2, 2021, provisional application No. 63/280,355, filed on Nov. 17, 2021.

(51) Int. Cl.
| | |
|---|---|
| *C07D 403/06* | (2006.01) |
| *A61K 31/4178* | (2006.01) |
| *A61P 11/00* | (2006.01) |
| *C07D 403/12* | (2006.01) |
| *C07D 417/06* | (2006.01) |

(52) U.S. Cl.
CPC ......... *C07D 403/06* (2013.01); *C07D 417/06* (2013.01)

(58) Field of Classification Search
CPC ................ C07D 403/06; C07D 403/12; A61K 31/4178; A61P 11/00
See application file for complete search history.

(56) References Cited

FOREIGN PATENT DOCUMENTS

WO   WO-2019183369 A1 *  9/2019   ........... C07D 233/84

OTHER PUBLICATIONS

Al-Ali et al., Scaffold Ranking and Positional Scanning Identify Novel Neurite Outgrowth Promoters with Nanomolar Potency, ACS Medicinal Chemistry Letters, vol. 9, No. 10, pp. 1057-1062 (Year: 2018).*
Nefzi et al., Synthesis of Dinydroimidazole Tethered Imidazolinethiones and Their Activity as Novel Antagonists of the Nuclear Retinoic Acid Receptor-Related Orphan Receptors (RORs), Bioorganic & Medicinal Chemistry Letters, vol. 27, No. 7, pp. 1608-1610 (Year: 2017).*
Acharya et al., Solid-Phase Synthesis of Substituted Imidazoline-Tethered 2,3-Diketopiperazines, Cyclic Ureas, and Cyclic Thioureas, Journal of Combinatorial Chemistry, vol. 3, No. 6, pp. 612-623 (Year: 2001).*
Adams J. W., et al., Enhanced Galphaq signaling: A common pathway mediates cardiac hypertrophy and apoptotic heart failure. Proc. Natl. Acad. Sci. U.S.A. 95, 10140-10145 (1998).
An, Steven S., et al. "Do biophysical properties of the airway smooth muscle in culture predict airway hyperresponsiveness?" American journal of respiratory cell and molecular biology 35.1 (2006): 55-64.
An, Steven S., et al. "TAS2R activation promotes airway smooth muscle relaxation despite β2-adrenergic receptor tachyphylaxis." American Journal of Physiology—Lung Cellular and Molecular Physiology 303.4 (2012): L304-L311.
Becke, Density-Functional Thermochemistry .3. The Role of Exact Exchange. J Chem Phys 98, 5648-5652 (1993).
Billington C. K., Penn R. B., Signaling and regulation of G protein-coupled receptors in airway smooth muscle. Respir. Res. 4, 2-24 (2003). *.
Bochevarov et al., Jaguar: A high-performance quantum chemistry software program with strengths in life and materials sciences. Int J Quantum Chem 113, 2110- 2142 (2013).
Booth H., Bish R., Walters J., Whitehead F., Walters E. H., Salmeterol tachyphylaxis in steroid treated asthmatic subjects. Thorax 51, 1100-1104 (1996).
Bussi, D. Donadio, M. Parrinello, Canonical sampling through velocity rescaling. J Chem Phys 126, 014101 (2007).
Cherezov et al., High-resolution crystal structure of an engineered human beta2-adrenergic G protein-coupled receptor. Science 318, 1258-1265 (2007).
Cheung D., et al., Long-term effects of a long-acting beta 2-adrenoceptor agonist, salmeterol, on airway hyperresponsiveness in patients with mild asthma. N. Engl. J. Med. 327, 1198-1203 (1992).
Choi M., et al., G protein-coupled receptor kinases (GRKs) orchestrate biased agonism at the β2-adrenergic receptor. Sci. Signal. 11, eaar7084 (2018).
Deshpande D. A., et al., Bitter taste receptors on airway smooth muscle bronchodilate by localized calcium signaling and reverse obstruction. Nat. Med. 16, 1299-1304 (2010).
DeWire S. M., et al. , A G protein-biased ligand at the μ-opioid receptor is potently analgesic with reduced gastrointestinal and respiratory dysfunction compared with morphine. J. Pharmacol. Exp. Ther. 344, 708-717 (2013).
Ditchfield, W. J. Hehre, J. A. Pople, Self-Consistent Molecular-Orbital Methods .9. Extended Gaussian-Type Basis for Molecular-Orbital Studies of Organic Molecules. J Chem Phys 54, 724-728 (1971).
Dooley C. T., Houghten R. A., New opioid peptides, peptidomimetics, and heterocyclic compounds from combinatorial libraries. Biopolymers 51, 379-390 (1999).
Dooley C. T., Ny P., Bidlack J. M., Houghten R. A., Selective ligands for the mu, delta, and kappa opioid receptors identified from a single mixture based tetrapeptide positional scanning combinatorial library. J. Biol. Chem. 273, 18848-18856 (1998).

(Continued)

*Primary Examiner* — Brenda L Coleman
(74) *Attorney, Agent, or Firm* — Meunier Carlin & Curfman LLC

(57) ABSTRACT

Disclosed herein are compounds, compositions, and methods for selecting targeting β$_2$AR receptors. The compounds, compositions, and methods may be used in the treatment of obstructive lung diseases.

14 Claims, 15 Drawing Sheets

(56) References Cited

OTHER PUBLICATIONS

Eason M. G., Jacinto M. T., Liggett S. B., Contribution of ligand structure to activation of a2AR subtype coupling to Gs. Mol. Pharmacol. 45, 696-702 (1994).

Eason M. G., Kurose H., Holt B. D., Raymond J. R., Liggett S. B., Simultaneous coupling of a2-adrenergic receptors to two G-proteins with opposing effects: Subtype-selective coupling of a2C10, a2C4 and a2C2 adrenergic receptors to Gi and Gs. J. Biol. Chem. 267, 15795-15801 (1992).

Eason M. G., Liggett S. B., Identification of a Gs coupling domain in the amino terminus of the third intracellular loop of the alpha 2A-adrenergic receptor. Evidence for distinct structural determinants that confer Gs versus Gi coupling. J. Biol. Chem. 270, 24753-24760 (1995).

Eason M. G., Moreira S. P., Liggett S. B., Four consecutive serines in the third intracellular loop are the sites for bARK-mediated phosphorylation and desensitization of the a2A-adrenergic receptor. J. Biol. Chem. 270, 4681-4688 (1995).

Eswar, et al., Protein structure modeling with Modeller. Methods Mol Biol 426, 145-159 (2008).

Goddard W. A. III, et al., Predicted 3D structures for adenosine receptors bound to ligands: Comparison to the crystal structure. J. Struct. Biol. 170, 10-20 (2010).

Grainger J., et al., Prescribed fenoterol and death from asthma in New Zealand, 1981-7: A further case-control study. Thorax 46, 105-111 (1991).

Green S. A., Liggett S. B., A proline-rich region of the third intracellular loop imparts phenotypic beta 1-versus beta 2-adrenergic receptor coupling and sequestration. J. Biol. Chem. 269, 26215-26219 (1994).

Griffith (2017) DarwinDock and GAG-Dock: Methods and Applications for Small Molecule Docking. in Chemistry and Chemical Engineering (California Institute of Technology, Pasadena, CA), p. 171.

Griffith A., "DarwinDock and GAG-Dock: Methods and applications for small molecule docking" PhD thesis, California Institute of Technology, Pasadena, CA: (2017).

Grove A., Lipworth B. J., Bronchodilator subsensitivity to salbutamol after twice daily salmeterol in asthmatic patients. Lancet 346, 201-206 (1995).

Hehre, J. A. Pople, Self-Consistent Molecular-Orbital Methods .13. Extended Gaussian-Type Basis for Boron. J Chem Phys 56, 4233-4234 (1972).

Heitzler D., et al., Competing G protein-coupled receptor kinases balance G protein and β-arrestin signaling. Mol. Syst. Biol. 8, 590 (2012).

Holloway A. C., et al., Side-chain substitutions within angiotensin II reveal different requirements for signaling, internalization, and phosphorylation of type 1A angiotensin receptors. Mol. Pharmacol. 61, 768-777 (2002).

Houghten R. A., et al. , Strategies for the use of mixture-based synthetic combinatorial libraries: Scaffold ranking, direct testing in vivo, and enhanced deconvolution by computational methods. J. Comb. Chem. 10, 3-19 (2008).

Israel E., et al.; National Heart, Lung, and Blood Institute's Asthma Clinical Research Network, Use of regularly scheduled albuterol treatment in asthma: Genotype-stratified, randomised, placebo-controlled cross-over trial. Lancet 364, 1505-1512 (2004).

Jewell-Motz E. A., Liggett S. B., G protein-coupled receptor kinase specificity for phosphorylation and desensitization of alpha2-adrenergic receptor subtypes. J. Biol. Chem. 271, 18082-18087 (1996).

Kalra S., Swystun V. A., Bhagat R., Cockcroft D. W., Inhaled corticosteroids do not prevent the development of tolerance to the bronchoprotective effect of salmeterol. Chest 109, 953-956 (1996).

Kenakin T., Biased receptor signaling in drug discovery. Pharmacol. Rev. 71, 267-315 (2019).

Kim D., et al. , Biased TAS2R bronchodilators inhibit airway smooth muscle growth by downregulating phosphorylated extracellular signal-regulated kinase 1/2. Am. J. Respir. Cell Mol. Biol. 60, 532-540 (2019).

Kim D., Pauer S. H., Yong H. M., An S. S., Liggett S. B., β2-adrenergic receptors chaperone trapped bitter taste receptor 14 to the cell surface as a heterodimer and exert unidirectional desensitization of taste receptor function. J. Biol. Chem. 291, 17616-17628 (2016).

Kim K. S., et al. , β-Arrestin-biased AT1R stimulation promotes cell survival during acute cardiac injury. Am. J. Physiol. Heart Circ. Physiol. 303, H1001-H1010 (2012).

Kim, L. Riley, R. Abrol, K. A. Jacobson, W. A. Goddard, 3rd, Predicted structures of agonist and antagonist bound complexes of adenosine A3 receptor. Proteins 79, 1878-1897 (2011).

Kraan J., Koëter G. H., vd Mark T. W., Sluiter H. J., de Vries K., Changes in bronchial hyperreactivity induced by 4 weeks of treatment with antiasthmatic drugs in patients with allergic asthma: A comparison between budesonide and terbutaline. J. Allergy Clin. Immunol. 76, 628-636 (1985).

Latorraca N. R., et al. , Molecular mechanism of GPCR-mediated arrestin activation. Nature 557, 452-456 (2018).

Lee, W. Yang, R. G. Parr, Development of the Colle-Salvetti correlation-energy formula into a functional of the electron density. Phys Rev B Condens Matter 37, 785-789 (1988).

Liggett S. B., Bitter taste receptors on airway smooth muscle as targets for novel bronchodilators. Expert Opin. Ther. Targets 17, 721-731 (2013).

Liggett S. B., Phosphorylation barcoding as a mechanism of directing GPCR signaling. Sci. Signal. 4, pe36 (2011).

Mafi A., Kim S. K., Goddard W. A. III, Mechanism of β-arrestin recruitment by the μ-opioid G protein-coupled receptor. Proc. Natl. Acad. Sci. U.S.A. 117, 16346-16355 (2020). -.

Mafi, S. K. Kim, W. A. Goddard, 3rd, The atomistic level structure for the activated human kappa-opioid receptor bound to the full Gi protein and the MP1104 agonist. Proc Natl Acad Sci U S A 117, 5836-5843 (2020).

Mark, L. Nilsson, Structure and dynamics of the TIP3P, SPC, and SPC/E water models at 298 K. J Phys Chem A 105, 9954-9960 (2001).

Monasky M. M., et al. , The β-arrestin-biased ligand TRV120023 inhibits angiotensin II-induced cardiac hypertrophy while preserving enhanced myofilament response to calcium. Am. J. Physiol. Heart Circ. Physiol. 305, H856-H866 (2013).

Motulsky H., Neubig R., Analyzing radioligand binding data. Curr. Protoc. Neurosci. Chapter 7, Unit 7.5 (2002).

Nelson H. S., Weiss S. T., Bleecker E. R., Yancey S. W., Dorinsky P. M .; SMART Study Group, The Salmeterol Multicenter Asthma Research Trial: A comparison of usual pharmacotherapy for asthma or usual pharmacotherapy plus salmeterol. Chest 129, 15-26 (2006).

Newnham D. M., Grove A., McDevitt D. G., Lipworth B. J., Tolerance of bronchodilator and systemic beta-2 adrenoceptor responses after regular twice daily treatment with eformoterol dry powder in asthmatic patients. Eur. Respir. J. 7, 235s (1994).

Olsen R. H. J., et al. , TRUPATH, an open-source biosensor platform for interrogating the GPCR transducerome. Nat. Chem. Biol. 16, 841-849 (2020).

Onaran et al., Systematic errors in detecting biased agonism: Analysis of current methods and development of a new model-free approach. Scientific reports 7, 44247 (2017).

Perry S. J., Lefkowitz R. J., Arresting developments in heptahelical receptor signaling and regulation. Trends Cell Biol. 12, 130-138 (2002).

Pettersen et al., UCSF Chimera—a visualization system for exploratory research and analysis. J Comput Chem 25, 1605-1612 (2004).

Piekielna-Ciesielska J., Wtorek K., Janecka A., Biased agonism as an emerging strategy in the search for better opioid analgesics. Curr. Med. Chem. 27, 1562-1575 (2020).

Rajagopal et al., Quantifying ligand bias at seven-transmembrane receptors. Mol Pharmacol 80, 367-377 (2011).

Rajagopal K., et al., Beta-arrestin2-mediated inotropic effects of the angiotensin II type 1A receptor in isolated cardiac myocytes. Proc. Natl. Acad. Sci. U.S.A. 103, 16284-16289 (2006).

Rasmussen et al., Crystal structure of the B2 adrenergic receptor-Gs protein complex. Nature 477, 549-555 (2011).

(56) References Cited

OTHER PUBLICATIONS

Rasmussen S. G., et al., Structure of a nanobody-stabilized active state of the β(2) adrenoceptor. Nature 469, 175-180 (2011).
Ring A. M., et al., Adrenaline-activated structure of β2-adrenoceptor stabilized by an engineered nanobody. Nature 502, 575-579 (2013).
Salpeter S. R., Wall A. J., Buckley N. S., Long-acting beta-agonists with and without inhaled corticosteroids and catastrophic asthma events. Am. J. Med. 123, 322-8.e2 (2010).
Santos R. G., et al., The mathematics of a successful deconvolution: A quantitative assessment of mixture-based combinatorial libraries screened against two formylpeptide receptors. Molecules 18, 6408-6424 (2013).
Seyedabadi M., Ghahremani M. H., Albert P. R., Biased signaling of G protein coupled receptors (GPCRs): Molecular determinants of GPCR/transducer selectivity and therapeutic potential. Pharmacol. Ther. 200, 148-178 (2019).
Shenoy S. K., et al., beta-arrestin-dependent, G protein-independent ERK1/2 activation by the beta2 adrenergic receptor. J. Biol. Chem. 281, 1261-1273 (2006).
Shukla A. K., et al., Visualization of arrestin recruitment by a G-protein-coupled receptor. Nature 512, 218-222 (2014).
Smith J. S., Lefkowitz R. J., Rajagopal S., Biased signalling: From simple switches to allosteric microprocessors. Nat. Rev. Drug Discov. 17, 243-260 (2018).
Sousa da Silva, W. F. Vranken, ACPYPE—AnteChamber PYthon Parser interfacE. BMC Res Notes 5, 367 (2012).
Staus D. P., et al., Sortase ligation enables homogeneous GPCR phosphorylation to reveal diversity in β-arrestin coupling. Proc. Natl. Acad. Sci. U.S.A. 115, 3834-3839 (2018).
Strachan R. T., et al., Divergent transducer-specific molecular efficacies generate biased agonism at a G protein-coupled receptor (GPCR). J. Biol. Chem. 289, 14211-14224 (2014).
Tak Kam, W. A. Goddard, 3rd, Flat-Bottom Strategy for Improved Accuracy in Protein Side-Chain Placements. J Chem Theory Comput 4, 2160-2169 (2008).
Urs N. M., et al., Distinct cortical and striatal actions of a β-arrestin-biased dopamine D2 receptor ligand reveal unique antipsychotic-like properties. Proc. Natl. Acad. Sci. U.S.A. 113, E8178-E8186 (2016).
Violin J. D., et al., Selectively engaging β-arrestins at the angiotensin II type 1 receptor reduces blood pressure and increases cardiac performance. J. Pharmacol. Exp. Ther. 335, 572-579 (2010).
Wang W. C., Mihlbachler K. A., Brunnett A. C., Liggett S. B., Targeted transgenesis reveals discrete attenuator functions of GRK and PKA in airway beta2-adrenergic receptor physiologic signaling. Proc. Natl. Acad. Sci. U.S.A. 106, 15007-15012 (2009).
Wei H., et al., Independent beta-arrestin 2 and G protein-mediated pathways for angiotensin II activation of extracellular signal-regulated kinases 1 and 2. Proc. Natl. Acad. Sci. U.S.A. 100, 10782-10787 (2003).
Weis W. I., Kobilka B. K., The molecular basis of G protein-coupled receptor activation. Annu. Rev. Biochem. 87, 897-919 (2018).
Wieland K., Zuurmond H. M., Krasel C., Ijzerman A. P., Lohse M. J., Involvement of Asn-293 in stereospecific agonist recognition and in activation of the beta 2-adrenergic receptor. Proc. Natl. Acad. Sci. U.S.A. 93, 9276-9281 (1996).
Wingler L. M., et al., Angiotensin and biased analogs induce structurally distinct active conformations within a GPCR. Science 367, 888-892 (2020).
Wisler J. W., et al., A unique mechanism of beta-blocker action: Carvedilol stimulates beta-arrestin signaling. Proc. Natl. Acad. Sci. U.S.A. 104, 16657-16662 (2007).
Wisler J. W., Xiao K., Thomsen A. R., Lefkowitz R. J., Recent developments in biased agonism. Curr. Opin. Cell Biol. 27, 18-24 (2014).
Woo J. A., et al., Differential long-term regulation of TAS2R14 by structurally distinct agonists. FASEB J. 33, 12213-12225 (2019).
Woo J. A., et al., β-Arrestin2 oligomers impair the clearance of pathological tau and increase tau aggregates. Proc. Natl. Acad. Sci. U.S.A. 117, 5006-5015 (2020).
Wu J., et al., Scaffold ranking and positional scanning utilized in the discovery of nAChR-selective compounds suitable for optimization studies. J. Med. Chem. 56, 10103-10117 (2013).
Xiao K., et al., Global phosphorylation analysis of beta-arrestin-mediated signaling downstream of a seven transmembrane receptor (7TMR). Proc. Natl. Acad. Sci. U.S.A. 107, 15299-15304 (2010).
Zhang X., et al., Identification of small molecules by screening a mixture-based scaffold compound library for treatment of alpha-1 antitrypsin deficiency. Biochem. Biophys. Res. Commun. 527, 317-323 (2020).

\* cited by examiner

BIASED ADRENERGIC AGONISTS

CROSS-REFERENCE TO RELATED APPLICATION

The Application claims the benefit of U.S. Provisional Applications 63/240,120, filed Sep. 2, 2021, and 63/280,355, filed Nov. 17, 2021, the contents of each are hereby incorporated in their entirety.

STATEMENT OF GOVERNMENT SUPPORT

This invention was made with government support under grant/contract number HL045967, HL155532, and HL114471, awarded by the National Institutes of Health. The government has certain rights in the invention.

FIELD OF THE INVENTION

The invention is directed to compounds, compositions, and methods for selecting targeting $\beta_2AR$ receptors. The compounds, compositions, and methods may be used in the treatment of obstructive lung diseases.

BACKGROUND

Most GPCRs are now recognized as multi-signal transducers. Early concepts of agonist-receptor interactions were based on the idea that there was a single "active" receptor conformation, induced by the binding of any agonist, resulting in an interaction with the heterotrimeric G protein, and a universal, singular, signal. Generally, the α-subunit of the G protein, upon its dissociation, was considered the primary activator (or inhibitor) of the effector, resulting in the intracellular signal. Subsequently, it became clear that multiple signaling outcomes from activation of a given GPCR can occur from a single agonist, due to specific molecular determinants of the receptor triggering independent mechanisms. As these multiple functions were being identified, it was apparent that agonists with different structures could act at a given receptor to preferentially activate one signal, with minimal engagement of others, a property later termed signal biasing. Biased agonists, then, could represent important advantages over nonbiased agonists due to this signal selectivity, activating a specified therapeutic pathway while minimally evoking unnecessary or deleterious signaling. The pathway selectivity of biased agonists is thought to be established by the stabilization of specific conformation(s) of the agonist-receptor complex via a set of interactions that differ from those of unbiased (also called balanced) agonists. While it is conceivable that small modifications of established cognate agonists might yield such specialized signaling, significant deviation from common agonist structures may be necessary to meet this goal.

The signals/functions of a given GPCR that might be sought for selective activation are defined by the cell type, disease, and desired final physiologic function. In asthma and chronic obstructive pulmonary disease (COPD), active human airway smooth muscle (HASM) cellular contraction limits airflow, representing a major cause of morbidity and mortality. β2ARs expressed on HASM cells are the targets for binding of therapeutically administered β-agonists, which relax the cells via a cAMP-mediated mechanism. β-agonists are used for treating acute bronchospasm as well as for long term prevention. However, the HASM bronchodilator response to acute β-agonist is attenuated by receptor desensitization, with typical treatments of humans, or HASM cells, leading to a loss of receptor function over time, clinically referred to as tachyphylaxis.

Agonist-promoted desensitization of β2AR (and other GPCRs) is due to partial uncoupling of the receptor to the G protein, which is initiated by phosphorylation of intracellular Ser/Thr residues of the receptor by G protein-coupled receptor kinases (GRKs). The GRK-phosphorylated β2AR recruits β-arrestin1 or β-arrestin2 to these receptors, with subsequent interactions that appear to compete with the receptor for its binding to the Gα subunit, thus attenuating the intracellular response. Such competition has been strongly inferred for the β2AR, and are compelling for rhodopsin-arrestin interactions. In addition, β-arrestin binding to GPCRs can initiate receptor internalization and other events such as receptor activation of ERK1/2, through its multiprotein adapter functions. Thus β-arrestin engagement can be considered an early "second signal" of the β2AR, as well as a desensitization initiator for attenuating the Gs signal. An agonist that is biased towards Gαs coupling (cAMP production and ASM relaxation) and away from β-arrestin binding (desensitization) would be desirable in treating obstructive lung diseases, since efficacy would not be attenuated acutely nor would tachyphylaxis be experienced from extended treatment. While biased agonists favoring either G protein or β-arrestin signaling have been described for some GPCRs (μ-opiate, angiotensin2 R1), Gαs biasing has not been apparent from most studies with catecholamine-like compounds for the β2AR. Thus, we have little information as to whether the two β2AR pathways can be differentially activated in a selective manner by an efficacious agonist, nor is it apparent from a structural standpoint what strategy might be employed to design agonists biased in this manner for this receptor.

There remains a need for improved, selective β2AR agonists. There remains a need for improved agonists selective for Gαs that do not interact with β-arrestin. There remains a need for improved methods of treating obstructive lung disorders, including asthma. There remains a need for improved agents for treating such obstructive lung disorders without inducing tachyphylaxis. The present invention addresses these needs. Additional advantages will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

The details of one or more embodiments are set forth in the descriptions below. Other features, objects, and advantages will be apparent from the description and from the claims.

DETAILED DESCRIPTION

Figure 1:
FIG. 1 depicts cAMP screening of a scaffold ranking (SR) library of 40 million compounds identifies a dihydroimidazolyl-butyl-cyclic urea scaffold containing β2AR agonists. 116 wells each containing mixtures of compounds (250 μg/ml) systematically arranged by scaffold type were used to treat cells transfected to express β2AR (CHW-β2 cells, lower row) and nontransfected CHW cells (upper row). The cAMP response for all wells is shown as a heat map indexed to the cAMP response to 10 μM forskolin using the color scheme shown. One well (SR library well 1319) increased cAMP in CHW-β2 cells >8 fold over basal levels (0.25% DMF vehicle). This mixture of compounds did not stimulate cAMP in the nontransfected CHW cells as indicated. Shown are mean results from two sets of determinations.
Figure 2A:
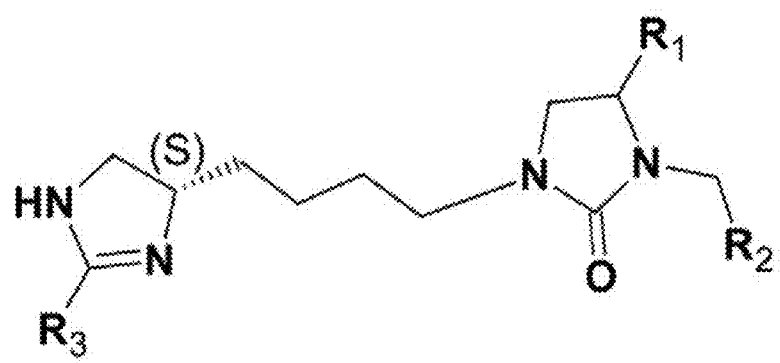
FIG. 2A depicts scaffold structure of compounds in SR library well 1319, with the indicated positions of groups denoted R1, R2, R3.
Figure 2B:
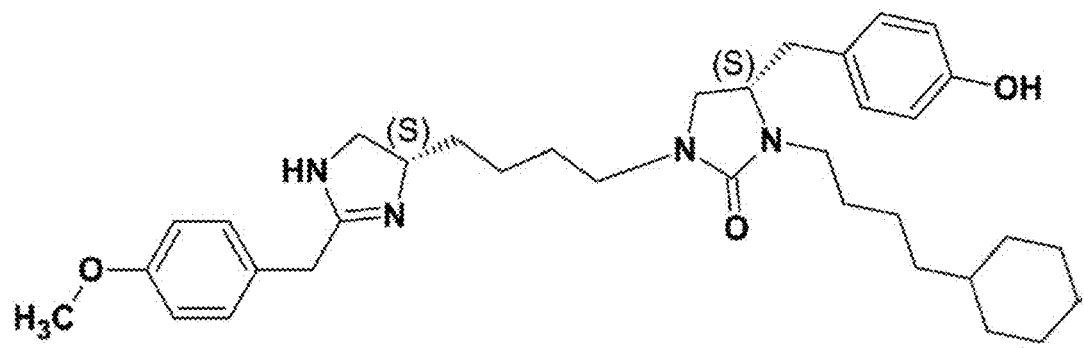
FIG. 2B depicts compound C1-S.
Figure 3:
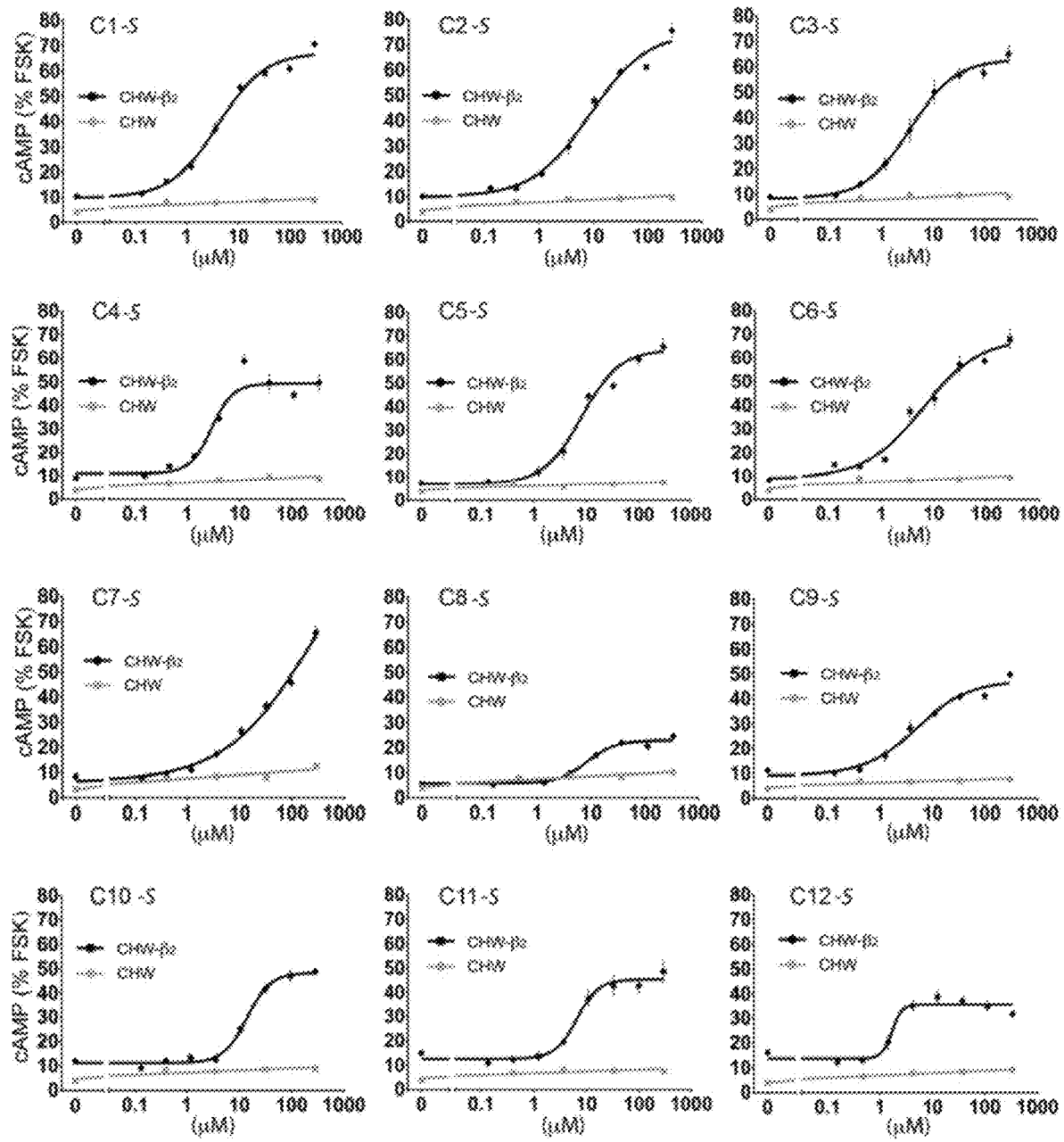
FIG. 3 depicts the pharmacologic properties of individual S- and R-stereoisomer compounds C1-C12. CHW-β2 cells were pretreated with vehicle or 10 μM of the $β_2AR$ antagonist propranolol for 5 min. Then the cAMP responses to 50 μM of the individual S-active compounds or their R-stereoisomers at the R1 position were determined. *, response to a compound (vehicle pretreated, black bars) is greater (P<0.01) than baseline (0.25% DMF); for all grey bars except for C7-S and C8-S, propranolol pretreatment resulted in no significant (P>0.05) stimulation by a compound over baseline; †, P<0.05 vs baseline. Results are mean±SE from 3 experiments.
Figure 4:
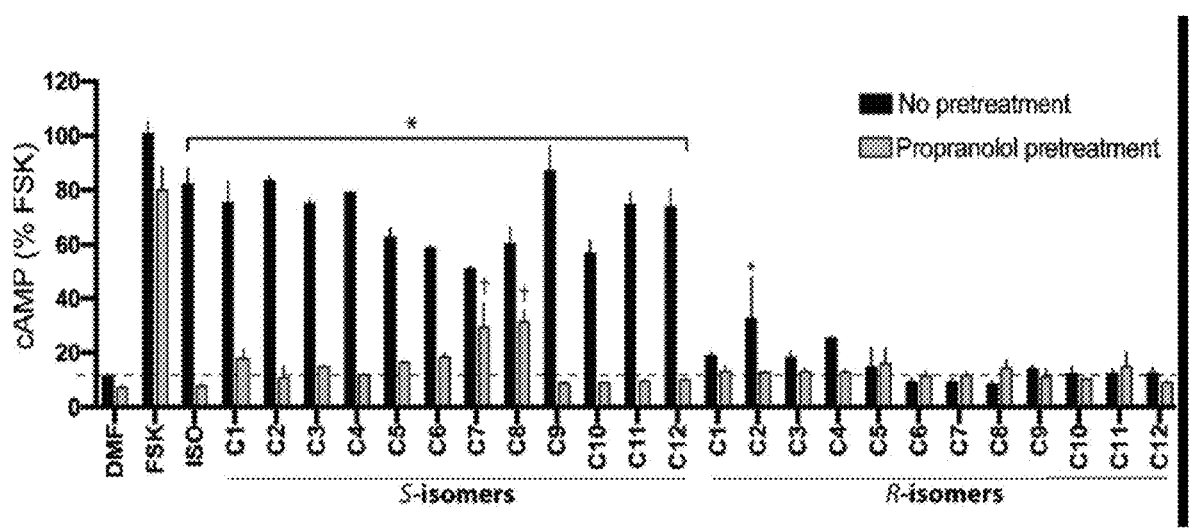
FIG. 4 depicts the agonist C1-S is biased towards $β_2AR$-Gαs interaction and away from $β_2AR$-βarrestin interaction.
Figure 5A:
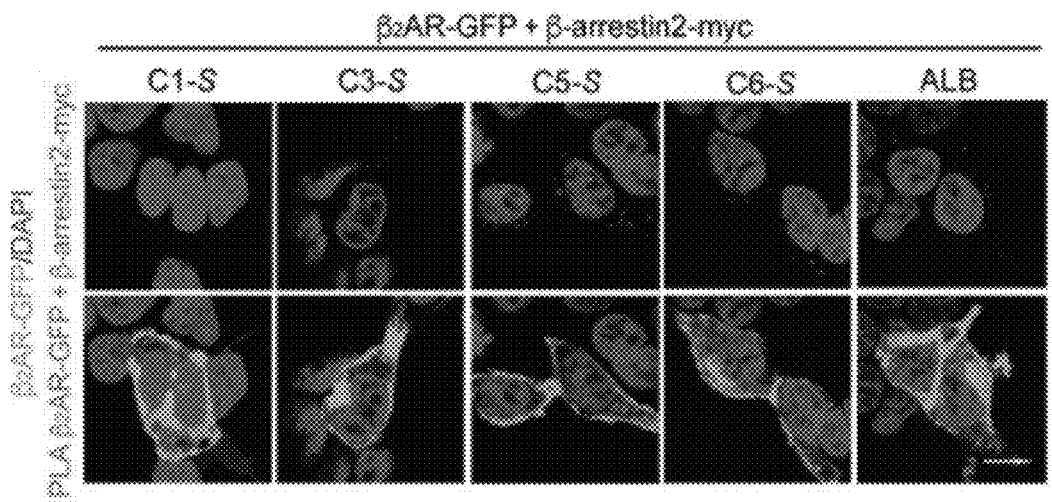
FIG. 5A depicts representative proximity ligation assay (PLA) results from transfected HEK-293 cells treated with the unbiased agonist albuterol (ALB, 10 mM) or the indicated compounds (300 mM). The top row depicts agonist-promoted close proximity of $β_2AR$-GFP and β-arrestin-2-myc, which was only found in cells that were expressing $β_2AR$-GFP (bottom row).
Figure 5B:
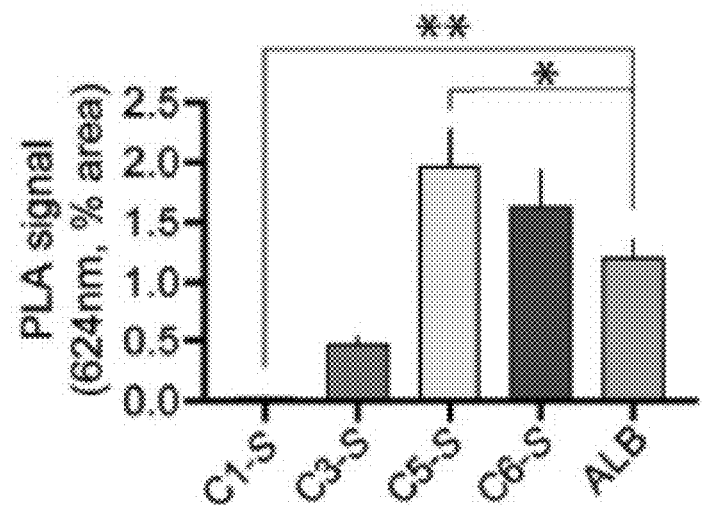
FIG. 5B depicts results from imaging in the red spectra from 5 independent PLA experiments at the same concentration of agonist as in FIG. 5A; PLA signal different than albuterol, * P<0.05, ** P<0.001.
Figure 5C:
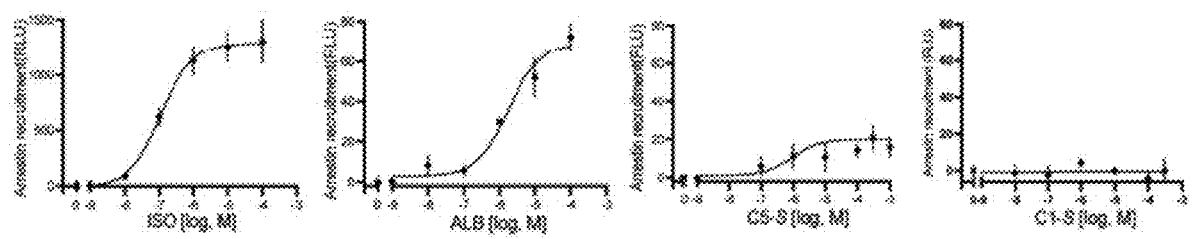
FIG. 5C depicts β-arrestin binding to $β_2AR$ as determined by the enzyme complementation assay (ECA). Response curves from isoproterenol (ISO), ALB, and C5-S showed concentration-dependent increases in the β-arrestin signal, while C1-S did not.
Figure 5D:
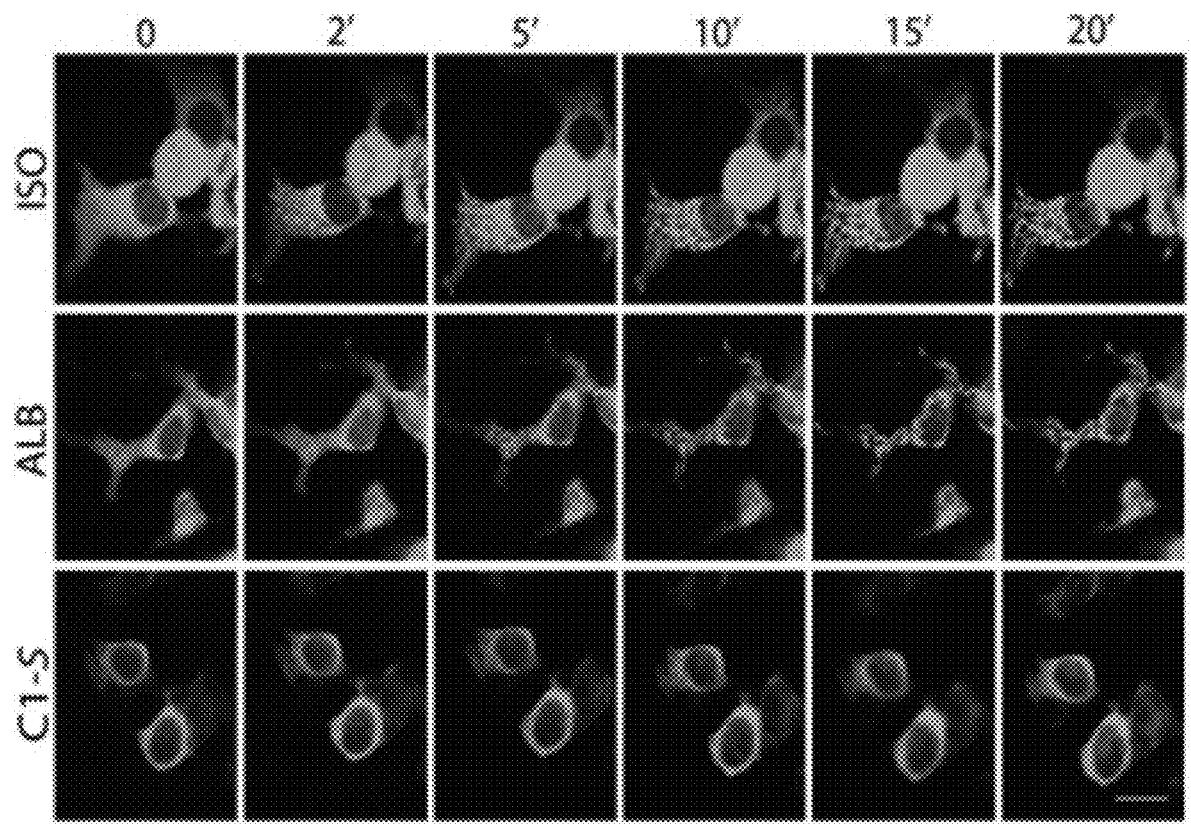
FIG. 5D depicts images of agonist-promoted recruitment of β-arrestin-GFP to cell surface puncta by the full PAR agonists ISO (1 mM) and the partial agonist ALB (10 mM), but not the partial agonist C1-S (300 mM). Image is representative of 4 experiments.
Figure 5E:
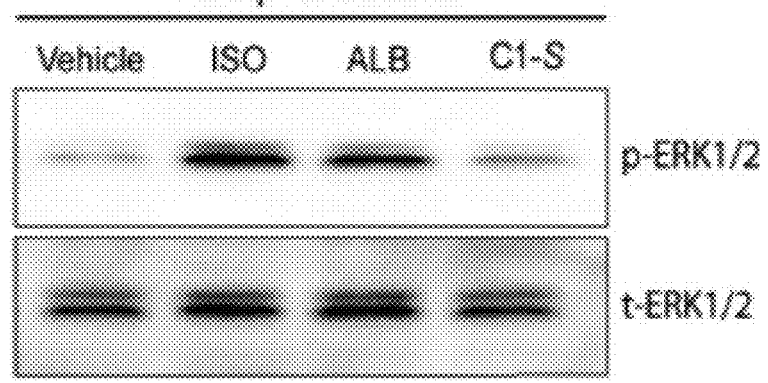
FIG. 5E depicts representative immunoblot of ERK1/2 activation by the indicated agonists in $β_2AR$ transfected HEK-293 cells in the presence of the PKA inhibitor H89.
Figure 5F:
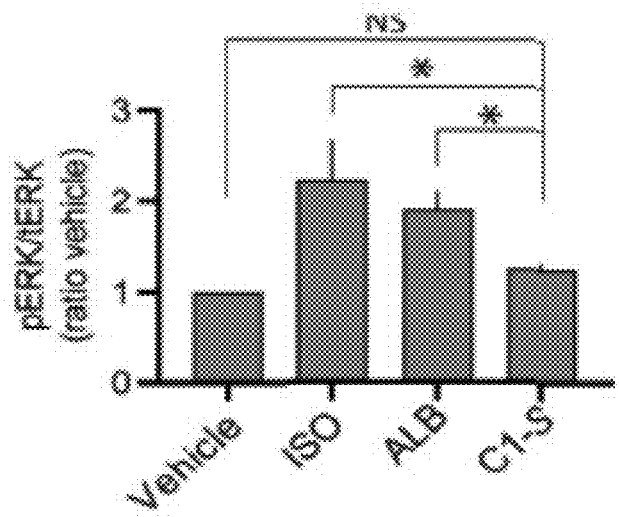
FIG. 5F depicts mean results of 5 independent experiments showing activation of ERK1/2 with isoproterenol and albuterol, but not C1-S, * P<0.05 vs vehicle control. Scaling bars in photomicrographs represent 10 μm.

Before the present methods and systems are disclosed and described, it is to be understood that the methods and systems are not limited to specific synthetic methods, specific components, or to particular compositions. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another embodiment includes-, from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal embodiment. "Such as" is not used in a restrictive sense, but for explanatory purposes.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

As used herein "aromatic" refers to an unsaturated cyclic molecule having 4n+2π electrons, wherein n is any integer. The term "non-aromatic" refers to any saturated system or unsaturated cyclic molecule which does not fall within the definition of aromatic.

The term "acyl" refers to groups —C(O)R, where R is hydrogen, alkyl, alkenyl, alkynyl, carbocyclyl, or heterocyclyl, as defined herein. Unless stated otherwise specifically in the specification, acyl can be optionally substituted.

"Alkyl" or "alkyl group" refers to a fully saturated, straight or branched hydrocarbon chain radical having from one to forty carbon atoms, and which is attached to the rest of the molecule by a single bond. Alkyls comprising any number of carbon atoms from 1 to 20 are included. An alkyl comprising up to 40 carbon atoms is a $C_1$-$C_{40}$ alkyl, an alkyl comprising up to 10 carbon atoms is a $C_1$-$C_{10}$ alkyl, an alkyl comprising up to 6 carbon atoms is a $C_1$-$C_6$ alkyl and an alkyl comprising up to 5 carbon atoms is a $C_1$-$C_5$ alkyl. A $C_1$-$C_5$ alkyl includes $C_5$ alkyls, $C_4$ alkyls, $C_3$ alkyls, $C_2$ alkyls and $C_1$ alkyl (i.e., methyl). A $C_1$-$C_6$ alkyl includes all moieties described above for $C_1$-$C_5$ alkyls but also includes $C_6$ alkyls. A $C_1$-$C_{10}$ alkyl includes all moieties described above for $C_1$-$C_5$ alkyls and $C_1$-$C_6$ alkyls, but also includes $C_7$, $C_8$, $C_9$ and $C_{10}$ alkyls. Similarly, a $C_1$-$C_{12}$ alkyl includes all the foregoing moieties, but also includes $C_{11}$ and $C_{12}$ alkyls. Non-limiting examples of $C_1$-$C_{12}$ alkyl include methyl, ethyl, n-propyl, i-propyl, sec-propyl, n-butyl, i-butyl, sec-butyl, t-butyl, n-pentyl, t-amyl, n-hexyl, n-heptyl, n-octyl, n-nonyl, n-decyl, n-undecyl, and n-dodecyl. Unless stated otherwise specifically in the specification, an alkyl group can be optionally substituted.

"Alkylene" or "alkylene chain" refers to a fully saturated, straight or branched divalent hydrocarbon chain radical, having from one to forty carbon atoms. Non-limiting examples of $C_2$-$C_{40}$ alkylene include ethylene, propylene, n-butylene, ethenylene, propenylene, n-butenylene, propynylene, n-butynylene, and the like. Unless stated otherwise specifically in the specification, an alkylene chain can be optionally substituted.

"Alkenyl" or "alkenyl group" refers to a straight or branched hydrocarbon chain radical having from two to forty carbon atoms, and having one or more carbon-carbon double bonds. Each alkenyl group is attached to the rest of the molecule by a single bond. Alkenyl group comprising any number of carbon atoms from 2 to 40 are included. An alkenyl group comprising up to 40 carbon atoms is a $C_2$-$C_{40}$ alkenyl, an alkenyl comprising up to 10 carbon atoms is a $C_2$-$C_{10}$ alkenyl, an alkenyl group comprising up to 6 carbon atoms is a $C_2$-$C_6$ alkenyl and an alkenyl comprising up to 5 carbon atoms is a $C_2$-$C_5$ alkenyl. A $C_2$-$C_5$ alkenyl includes $C_5$ alkenyls, $C_4$ alkenyls, $C_3$ alkenyls, and $C_2$ alkenyls. A $C_2$-$C_6$ alkenyl includes all moieties described above for $C_2$-$C_5$ alkenyls but also includes $C_6$ alkenyls. A $C_2$-$C_{10}$ alkenyl includes all moieties described above for $C_2$-$C_5$ alkenyls and $C_2$-$C_6$ alkenyls, but also includes $C_7$, $C_8$, $C_9$ and $C_{10}$ alkenyls. Similarly, a $C_2$-$C_{12}$ alkenyl includes all the foregoing moieties, but also includes $C_{11}$ and $C_{12}$ alkenyls. Non-limiting examples of $C_2$-$C_{12}$ alkenyl include ethenyl (vinyl), 1-propenyl, 2-propenyl (allyl), iso-propenyl, 2-methyl-1-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8-decenyl, 9-decenyl, 1-undecenyl, 2-undecenyl, 3-undecenyl, 4-undecenyl, 5-undecenyl, 6-undecenyl, 7-undecenyl, 8-undecenyl, 9-undecenyl, 10-undecenyl, 1-dodecenyl, 2-dodecenyl, 3-dodecenyl, 4-dodecenyl, 5-dodecenyl, 6-dodecenyl, 7-dodecenyl, 8-dodecenyl, 9-dodecenyl, 10-dodecenyl, and 11-dodecenyl. Unless stated otherwise specifically in the specification, an alkyl group can be optionally substituted.

"Alkenylene" or "alkenylene chain" refers to a straight or branched divalent hydrocarbon chain radical, having from two to forty carbon atoms, and having one or more carbon-carbon double bonds. Non-limiting examples of $C_2$-$C_{40}$ alkenylene include ethene, propene, butene, and the like. Unless stated otherwise specifically in the specification, an alkenylene chain can be optionally.

"Alkoxy" refers to the group —OR, where R is alkyl, alkenyl, alkynyl, cycloalkyl, or heterocyclyl as defined herein. Unless stated otherwise specifically in the specification, alkoxy can be optionally substituted.

"Alkylcarbamoyl" refers to the group —O—C(O)—$NR_aR_b$, where $R_a$ and $R_b$ are the same or different and independently an alkyl, alkenyl, alkynyl, aryl, heteroaryl, cycloalkyl, or heterocyclyl group, as defined herein, or $R_aR_b$ can be taken together to form a heterocyclyl group, as defined herein. Unless stated otherwise specifically in the specification, alkylcarbamoyl can be optionally substituted.

"Alkylcarboxamidyl" refers to the group —C(O)—$NR_aR_b$, where $R_a$ and $R_b$ are the same or different and independently an alkyl, alkenyl, alkynyl, aryl, heteroaryl, cycloalkyl, cycloalkenyl, cycloalkynyl, or heterocyclyl group, as defined herein, or $R_aR_b$ can be taken together to form a cycloalkyl group, as defined herein. Unless stated otherwise specifically in the specification, alkylcarboxamidyl can be optionally substituted.

"Alkoxycarbonyl" refers to the group —C(O)OR, where R is alkyl, alkenyl, alkynyl, aryl, heteroaryl, cycloalkyl, cycloalkenyl, cycloalkynyl, or heterocyclyl group, as defined herein. Unless stated otherwise specifically in the specification, alkoxycarbonyl can be optionally substituted.

"Alkylthio" refers to the —SR or —S(O)$_{n=1-2}$—R, where R is alkyl, alkenyl, alkynyl, cycloalkyl, cycloalkenyl, cycloalkynyl, or hetereocyclyl, as defined herein. Unless stated otherwise specifically in the specification, alkylthio can be optionally substituted.

"Arylthio" refers to the —SR or —S(O)$_{n=1-2}$—R, where R is aryl or heteroaryl, as defined herein. Unless stated otherwise specifically in the specification, arylthio can be optionally substituted.

"Alkynyl" or "alkynyl group" refers to a straight or branched hydrocarbon chain radical having from two to forty carbon atoms, and having one or more carbon-carbon triple bonds. Each alkynyl group is attached to the rest of the molecule by a single bond. Alkynyl group comprising any number of carbon atoms from 2 to 40 are included. An alkynyl group comprising up to 40 carbon atoms is a $C_2$-$C_{40}$ alkynyl, an alkynyl comprising up to 10 carbon atoms is a $C_2$-$C_{10}$ alkynyl, an alkynyl group comprising up to 6 carbon atoms is a $C_2$-$C_6$ alkynyl and an alkynyl comprising up to 5 carbon atoms is a $C_2$-$C_5$ alkynyl. A $C_2$-$C_5$ alkynyl includes $C_5$ alkynyls, $C_4$ alkynyls, $C_3$ alkynyls, and $C_2$ alkynyls. A $C_2$-$C_6$ alkynyl includes all moieties described above for $C_2$-$C_5$ alkynyls but also includes $C_6$ alkynyls. A $C_2$-$C_{10}$ alkynyl includes all moieties described above for $C_2$-$C_5$ alkynyls and $C_2$-$C_6$ alkynyls, but also includes $C_7$, $C_8$, $C_9$ and $C_{10}$ alkynyls. Similarly, a $C_2$-$C_{12}$ alkynyl includes all the foregoing moieties, but also includes $C_{11}$ and $C_{12}$ alkynyls. Non-limiting examples of $C_2$-$C_{12}$ alkenyl include ethynyl, propynyl, butynyl, pentynyl and the like. Unless stated otherwise specifically in the specification, an alkyl group can be optionally substituted.

"Alkynylene" or "alkynylene chain" refers to a straight or branched divalent hydrocarbon chain, having from two to forty carbon atoms, and having one or more carbon-carbon triple bonds. Non-limiting examples of $C_2$-$C_{40}$ alkynylene include ethynylene, propargylene and the like. Unless stated otherwise specifically in the specification, an alkynylene chain can be optionally substituted.

"Carbocyclyl," "carbocyclic ring" or "carbocycle" refers to a rings structure, wherein the atoms which form the ring are each carbon. Carbocyclic rings can comprise from 3 to 20 carbon atoms in the ring. Unless stated otherwise specifically in the specification, the carbocyclyl can be a monocyclic, bicyclic, tricyclic or tetracyclic ring system, which can include fused or bridged ring systems Carbocyclic rings include cycloalkyl, cycloalkenyl, and cycloalkynyl as defined herein. In some embodiments, the carbocyclyl is monovalent and is attached to the rest of molecule through a single bond. In some embodiments, the carbocyclyl is divalent and is independently attached to two moieties through single bonds. Unless stated otherwise specifically in the specification, a carbocyclyl group can be optionally substituted.

"Cycloalkyl" refers to a stable non-aromatic monocyclic or polycyclic fully saturated hydrocarbon radical consisting solely of carbon and hydrogen atoms, which can include fused or bridged ring systems, having from three to twenty carbon atoms, preferably having from three to ten carbon atoms, and which is attached to the rest of the molecule by a single bond. Monocyclic cycloalkyl radicals include, for example, cyclopropyl, cyclobutyl, cyclopentyl, cyclohexyl, cycloheptyl, and cyclooctyl. Polycyclic cycloalkyl radicals include, for example, adamantyl, norbornyl, decalinyl, 7,7-dimethyl-bicyclo[2.2.1]heptanyl, and the like. Unless otherwise stated specifically in the specification, a cycloalkyl group can be optionally substituted.

"Cycloalkenyl" refers to a stable non-aromatic monocyclic or polycyclic hydrocarbon radical consisting solely of carbon and hydrogen atoms, having one or more carbon-carbon double bonds, which can include fused or bridged ring systems, having from three to twenty carbon atoms, preferably having from three to ten carbon atoms, and which is attached to the rest of the molecule by a single bond. Monocyclic cycloalkenyl radicals include, for example, cyclopentenyl, cyclohexenyl, cycloheptenyl, cyclooctenyl, and the like. Polycyclic cycloalkenyl radicals include, for example, bicyclo[2.2.1]hept-2-enyl and the like. Unless otherwise stated specifically in the specification, a cycloalkenyl group can be optionally substituted.

"Cycloalkynyl" refers to a stable non-aromatic monocyclic or polycyclic hydrocarbon radical consisting solely of carbon and hydrogen atoms, having one or more carbon-carbon triple bonds, which can include fused or bridged ring systems, having from three to twenty carbon atoms, preferably having from three to ten carbon atoms, and which is attached to the rest of the molecule by a single bond. Monocyclic cycloalkynyl radicals include, for example, cycloheptynyl, cyclooctynyl, and the like. Unless otherwise stated specifically in the specification, a cycloalkynyl group can be optionally substituted.

"Heterocyclyl," "heterocyclic ring" or "heterocycle" refers to a stable 3- to 20-membered ring radical, which consists of two to fourteen carbon atoms and from one to eight heteroatoms selected from the group consisting of nitrogen, oxygen and sulfur. Unless stated otherwise specifically in the specification, the heterocyclyl radical can be a monocyclic, bicyclic, tricyclic or tetracyclic ring system, which can include fused or bridged ring systems; and the nitrogen, carbon or sulfur atoms in the heterocyclyl radical can be optionally oxidized; the nitrogen atom can be optionally quaternized; and the heterocyclyl radical can be aromatic, partially saturated, or fully saturated. Examples of heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxothiomorpholinyl. In some embodiments, the heterocyclyl is monovalent and is attached to the rest of molecule through a single bond. In some embodiments, the heterocyclyl is divalent and is independently attached to two moieties through single bonds. Unless stated otherwise specifically in the specification, a heterocyclyl group can be optionally substituted.

"Aryl" refers to a hydrocarbon ring system radical comprising hydrogen, 6 to 18 carbon atoms and at least one aromatic ring. For purposes of this invention, the aryl radical can be a monocyclic, bicyclic, tricyclic or tetracyclic ring system, which can include fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" is meant to include aryl radicals that are optionally substituted.

"Aryloxy" refers to groups —OAr, where Ar is an aryl or heteroaryl group as defined herein. Unless otherwise stated specifically in the specification, the aryloxy group can be optionally substituted.

"Heteroaryl" refers to a 5- to 20-membered ring system radical comprising hydrogen atoms, one to thirteen carbon atoms, one to six heteroatoms selected from the group consisting of nitrogen, oxygen and sulfur, and at least one aromatic ring. For purposes of this invention, the heteroaryl radical can be a monocyclic, bicyclic, tricyclic or tetracyclic ring system, which can include fused or bridged ring systems; and the nitrogen, carbon or sulfur atoms in the heteroaryl radical can be optionally oxidized; the nitrogen atom can be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e. thienyl). Unless stated otherwise specifically in the specification, a heteroaryl group can be optionally substituted.

A radical preceded by the term "$C_{x-x}$alk" refers to that radical connected via an alkylene chain of the specified length. By way of example, "—$C_{3-10}$cycloalkyl" refers to a group having a $C_{3-10}$cycloalkyl connected via a $C_{1-8}$alkylene chain. Similarly, $C_{1-8}$alk-aryl refers to an aryl group connected via a $C_{1-8}$alkylene chain.

The term "substituted" used herein means any of the above groups (i.e., alkyl, alkenyl, alkynyl, cycloalkyl, cycloalkenyl, cycloalkynyl, heterocyclyl, aryl, heteroaryl, alkoxy, aryloxy, acyl, alkylcarbamoyl, alkylcarboxamidyl, alkoxycarbonyl, alkylthio, or arylthio) wherein at least one atom is replaced by a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more atoms are replaced with —$NR_gR_h$, —$NR_gC(=O)R_h$, —$NR_gC(=O)NR_gR_h$, —$NR_gC(=O)OR_h$, —$NR_gSO_2R_h$, —$OC(=O)NR_gR_h$, —$OR_g$, —$SR_g$, —$SOR_g$, —$SO_2R_g$, —$OSO_2R_g$, —$SO_2OR_g$, =$NSO_2R_g$, and —$SO_2NR_gR_h$. "Substituted also means any of the above groups in which one or more hydrogen atoms are replaced with —$C(=O)R_g$, —$C(=O)OR_g$, —$C(=O)NR_gR_h$, —$CH_2SO_2R_g$, —$CH_2SO_2NR_gR_h$. In the foregoing, $R_g$ and $R_h$ are the same or different and independently hydrogen, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl. "Substituted" further means any of the above groups in which one or more atoms are replaced by an amino, cyano, hydroxyl, imino, nitro, oxo, thioxo, halo, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl group. "Substituted" can also mean an amino acid in which one or more atoms on the side chain are replaced by alkyl, alkenyl, alkynyl, acyl, alkylcarboxamidyl, alkoxycarbonyl, carbocyclyl, heterocyclyl, aryl, or heteroaryl. In addition, each of the foregoing substituents can also be optionally substituted with one or more of the above substituents.

Unless stated to the contrary, a formula with chemical bonds shown only as solid lines and not as wedges or dashed lines contemplates each possible isomer, e.g., each enantiomer, diastereomer, and meso compound, and a mixture of isomers, such as a racemic or scalemic mixture. Unless stated to the contrary, a formula depicting one or more stereochemical features does not exclude the presence of other isomers.

Unless stated to the contrary, a substituent drawn without explicitly specifying the point of attachment indicates that the substituent may be attached at any possible atom. For example, in a benzofuran depicted as:

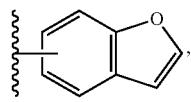

the substituent may be present at any one of the six possible carbon atoms.

As used herein, the term "null," when referring to a possible identity of a chemical moiety, indicates that the group is absent, and the two adjacent groups are directly bonded to one another. By way of example, for a genus of compounds having the formula $CH_3$—X—$CH_3$, if X is null, then the resulting compound has the formula $CH_3$—$CH_3$.

Pharmaceutically acceptable salts are salts that retain the desired biological activity of the parent compound and do not impart undesirable toxicological effects. Examples of such salts are acid addition salts formed with inorganic acids, for example, hydrochloric, hydrobromic, sulfuric, phosphoric, and nitric acids and the like; salts formed with organic acids such as acetic, oxalic, tartaric, succinic, maleic, fumaric, gluconic, citric, malic, methanesulfonic, p-toluenesulfonic, napthalenesulfonic, and polygalacturonic acids, and the like; salts formed from elemental anions such as chloride, bromide, and iodide; salts formed from metal hydroxides, for example, sodium hydroxide, potassium hydroxide, calcium hydroxide, lithium hydroxide, and magnesium hydroxide; salts formed from metal carbonates, for example, sodium carbonate, potassium carbonate, calcium carbonate, and magnesium carbonate; salts formed from metal bicarbonates, for example, sodium bicarbonate and potassium bicarbonate; salts formed from metal sulfates, for example, sodium sulfate and potassium sulfate; and salts formed from metal nitrates, for example, sodium nitrate and potassium nitrate. Pharmaceutically acceptable and non-pharmaceutically acceptable salts may be prepared using procedures well known in the art, for example, by reacting a sufficiently basic compound such as an amine with a suitable acid comprising a physiologically acceptable anion. Alkali metal (for example, sodium, potassium, or lithium) or alkaline earth metal (for example, calcium) salts of carboxylic acids can also be made.

As used herein, the term "about" or "approximately" refers to a quantity, level, value, number, frequency, percentage, dimension, size, amount, weight or length that varies by acceptable levels in the art. In some embodiments, the amount of variation may be as much as 15%, 10%, 9%, 8%, 7%, 6%, 5%, 4%, 3%, 2% or 1% to a reference quantity, level, value, number, frequency, percentage, dimension, size, amount, weight or length. In one embodiment, the term "about" or "approximately" refers a range of quantity, level, value, number, frequency, percentage, dimension, size, amount, weight or length ±15%, ±10%, ±9%, ±8%, ±7%, ±6%, ±5%, ±4%, ±3%, ±2%, or ±1% about a reference quantity, level, value, number, frequency, percentage, dimension, size, amount, weight or length.

A numerical range, e.g., 1 to 5, about 1 to 5, or about 1 to about 5, refers to each numerical value encompassed by the range. For example, in one non-limiting and merely illustrative embodiment, the range "1 to 5" is equivalent to the expression 1, 2, 3, 4, 5; or 1.0, 1.5, 2.0, 2.5, 3.0, 3.5, 4.0, 4.5, or 5.0; or 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5.0.

As used herein, the term "substantially" refers to a quantity, level, value, number, frequency, percentage, dimension, size, amount, weight or length that is 80%, 85%, 90%, 91%, 92%, 93%, 94%, 95%, 96%, 97%, 98%, 99% or higher compared to a reference quantity, level, value, number, frequency, percentage, dimension, size, amount, weight or length. In one embodiment, "substantially the same" refers to a quantity, level, value, number, frequency, percentage, dimension, size, amount, weight or length that produces an effect, e.g., a physiological effect, that is approximately the same as a reference quantity, level, value, number, frequency, percentage, dimension, size, amount, weight or length.

Disclosed herein are Gαs-biased β$_2$AR agonists. As used herein, a Gαs-biased β$_2$AR agonist has decreased agonizing activity towards β-arrestin while still stimulating cAMP. In some instances, the biased agonists have the formula:

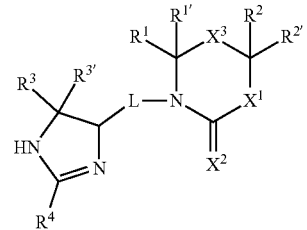

or a pharmaceutically acceptable salt thereof, wherein:

$R^1$ is selected from $Z^1$—$R^{1a}$, $Z^1$—$OR^{1a}$, $Z^1$—$N(R^{1a})_2$, $Z^1$—$C(O)R^{1a}$, $Z^1$—$C(O)OR^{1a}$, $Z^1$—$OCOR^{1a}$, $Z^1$—$C(O)N(R^{1a})_2$, F, Cl, Br, I, cyano, and nitro, wherein $R^{1a}$ is in each case independently selected from hydrogen, $C_{1-8}$alkyl, $C_{2-8}$alkenyl, $C_{2-8}$alkynyl, aryl, $C_{1-8}$heteroaryl, $C_{3-8}$cycloalkyl, or $C_{1-8}$heterocyclyl; and $Z^1$ is —$(CH_2)_{n1}$— wherein n1 is 0-6;

$R^{1'}$ is selected from $Z^{1'}$—$R^{1a'}$, $Z^{1'}$—$OR^{1a'}$, $Z^{1'}$—$N(R^{1a'})_2$, $Z^{1'}$—$C(O)R^{1a'}$, $Z^{1'}$—$C(O)OR^{1a'}$, $Z^{1'}$—$OCOR^{1a'}$, $Z^{1'}$—$C(O)N(R^{1a'})_2$, F, Cl, Br, I, cyano, and nitro, wherein $R^{1a'}$ is in each case independently selected from hydrogen, $C_{1-8}$alkyl, $C_{2-8}$alkenyl, $C_{2-8}$alkynyl, aryl, $C_{1-8}$heteroaryl, $C_{3-8}$cycloalkyl, or $C_{1-8}$heterocyclyl; and $Z^{1'}$ is —$(CH_2)_{n1'}$— wherein n1' is 0-6;

R² is selected from Z²—R²ᵃ, Z²—OR²ᵃ, Z²—N(R²ᵃ)₂, Z²—C(O)R²ᵃ, Z²—C(O)OR²ᵃ, Z²—OCOR²ᵃ, Z²—C(O)N(R²ᵃ)₂, F, Cl, Br, I, cyano, and nitro, wherein R²ᵃ is in each case independently selected from hydrogen, C₁₋₈alkyl, C₂₋₈alkenyl, C₂₋₈alkynyl, aryl, C₁₋₈heteroaryl, C₃₋₈cycloalkyl, or C₁₋₈heterocyclyl; and Z² is —(CH₂)ₙ₂— wherein n2 is 0-6;

R²' is selected from Z²'—R²ᵃ', Z²'—OR²ᵃ', Z²'—N(R²ᵃ')₂, Z²'—C(O)R²ᵃ', Z²'—C(O)OR²ᵃ', Z²'—OCOR²ᵃ', Z²'—C(O)N(R²ᵃ')₂, F, Cl, Br, I, cyano, and nitro, wherein R²ᵃ' is in each case independently selected from hydrogen, C₁₋₈alkyl, C₂₋₈alkenyl, C₂₋₈alkynyl, aryl, C₁₋₈heteroaryl, C₃₋₈cycloalkyl, or C₁₋₈heterocyclyl; and Z²' is —(CH₂)ₙ₂'— wherein n2' is 0-6;

R³ is selected from Z³—R³ᵃ, Z³—OR³ᵃ, Z³—N(R³ᵃ)₂, Z³—C(O)R³ᵃ, Z³—C(O)OR³ᵃ, Z³—OCOR³ᵃ, Z³—C(O)N(R³ᵃ)₂, F, Cl, Br, I, cyano, and nitro, wherein R³ᵃ is in each case independently selected from hydrogen, C₁₋₈alkyl, C₂₋₈alkenyl, C₂₋₈alkynyl, aryl, C₁₋₈heteroaryl, C₃₋₈cycloalkyl, or C₁₋₈heterocyclyl; and Z³ is —(CH₂)ₙ₃— wherein n3 is 0-6;

R³' is selected from Z³'—R³ᵃ', Z³'—OR³ᵃ', Z³'—N(R³ᵃ')₂, Z³'—C(O)R³ᵃ', Z³'—C(O)OR³ᵃ', Z³'—OCOR³ᵃ', Z³'—C(O)N(R³ᵃ')₂, F, Cl, Br, I, cyano, and nitro, wherein R³ᵃ' is in each case independently selected from hydrogen, C₁₋₈alkyl, C₂₋₈alkenyl, C₂₋₈alkynyl, aryl, C₁₋₈heteroaryl, C₃₋₈cycloalkyl, or C₁₋₈heterocyclyl; and Z³' is —(CH₂)ₙ₃'— wherein n3' is 0-6;

R⁴ is selected from Z⁴—R⁴ᵃ, Z⁴—OR⁴ᵃ, Z⁴—N(R⁴ᵃ)₂, Z⁴—C(O)R⁴ᵃ, Z⁴—C(O)OR⁴ᵃ, Z⁴—OCOR⁴ᵃ, Z⁴—C(O)N(R⁴ᵃ)₂, F, Cl, Br, I, cyano, and nitro, wherein R⁴ᵃ is in each case independently selected from hydrogen, C₁₋₈alkyl, C₂₋₈alkenyl, C₂₋₈alkynyl, aryl, C₁₋₈heteroaryl, C₃₋₈cycloalkyl, or C₁₋₈heterocyclyl; and Z⁴ is —(CH₂)ₙ₄— wherein n4 is 0-6;

L is an optionally substituted alkylene, carbocyclic, heterocyclyl, aryl, or heteroaryl, X¹ is selected from O, CHR⁵, and NR⁵, wherein R⁵ is selected from H, C₁₋₈alkyl, C₂₋₈alkenyl, C₂₋₈alkynyl, C₃₋₁₀cycloalkyl, aryl, heteroaryl, C₁₋₈alk-C₃₋₁₀cycloalkyl, C₁₋₈alk-aryl, C₁₋₆heterocyclyl, C₁₋₈alk-heteroaryl, and C₁₋₈alk-C₁₋₆heterocyclyl;

X² is selected from S and O;

X³ is selected from a bond or —CR⁶R⁶'—, wherein

R⁶ is selected from Z⁶—R⁶ᵃ, Z⁶—OR⁶ᵃ, Z⁶—N(R⁶ᵃ)₂, Z⁶—C(O)R⁶ᵃ, Z⁶—C(O)OR⁶ᵃ, Z⁶—OCOR⁶ᵃ, Z⁶—C(O)N(R⁶ᵃ)₂, F, Cl, Br, I, cyano, and nitro, wherein R⁶ᵃ is in each case independently selected from hydrogen, C₁₋₈alkyl, C₂₋₈alkenyl, C₂₋₈alkynyl, aryl, C₁₋₈heteroaryl, C₃₋₈cycloalkyl, or C₁₋₈heterocyclyl; and Z⁶ is null or —(CH₂)ₙ₆— wherein n6 is 1-6;

R⁶' is selected from Z⁶'—R⁶'ᵃ, Z⁶'—OR⁶'ᵃ, Z⁶'—N(R⁶'ᵃ)₂, Z⁶'—C(O)R⁶'ᵃ; Z⁶'—C(O)OR⁶'ᵃ, Z⁶'—OCOR⁶'ᵃ; Z⁶'—C(O)N(R⁶'ᵃ)₂, F, Cl, Br, I, cyano, and nitro, wherein R⁶'ᵃ is in each case independently selected from hydrogen, C₁₋₈alkyl, C₂₋₈alkenyl, C₂₋₈alkynyl, aryl, C₁₋₈heteroaryl, C₃₋₈cycloalkyl, or C₁₋₈heterocyclyl; and Z⁶' is null or —(CH₂)ₙ₆'— wherein n6' is 1-6;

wherein any two or more of R¹, R¹', R², R²', R³, R³', R⁴, R⁵, R⁶, or R⁶' may together form a ring.

In certain embodiments, L is —(CH₂)ₗ₁—, —(CH₂)ₗ₂O(CH₂)ₗ₂—, or —(CH₂)ₗ₂NR^L(CH₂)ₗ₂—;

wherein L1 and L2 is in each case independently selected from 0-4; and R^L is H or C₁₋₄alkyl. In some embodiments L may be substituted one or more times, or can include an embedded ring.

In some instances, the linker can be attached to the dihydroimidazole ring in the following stereochemical configuration.

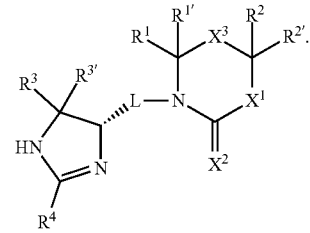

In preferred embodiments, X² is O.

In some embodiments, the disclosed compounds can include a bicyclic moiety, e.g., a compound having the formula:

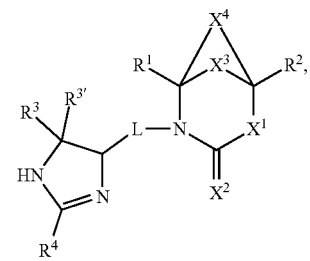

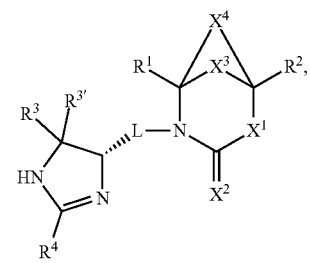

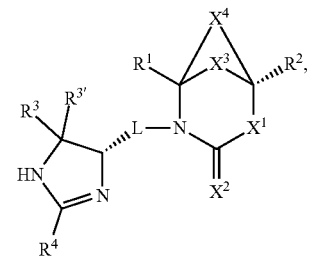

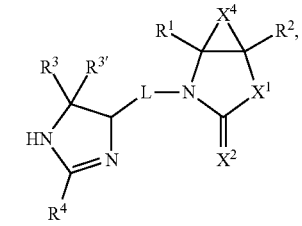

-continued

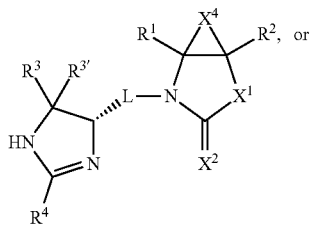

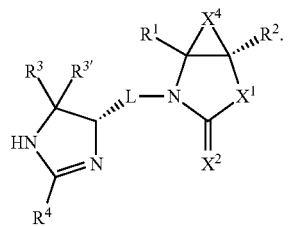

wherein $X^4$ is —$(CH_2)_{n7}$—, —$(CH_2)_{n8}O(CH_2)_{n8}$—, or —$(CH_2)_{n8}NR^7(CH_2)_{n8}$—, wherein n7 is 1-6 and n8 is in each case independently selected from 0-4; and $R^7$ is H or $C_{1-4}$alkyl.

Exemplary bicyclic moieties include:

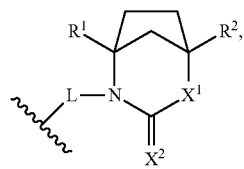 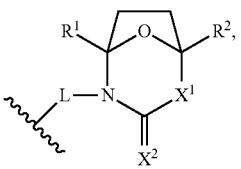

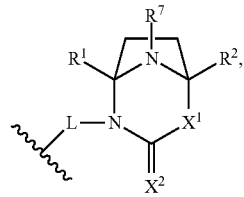 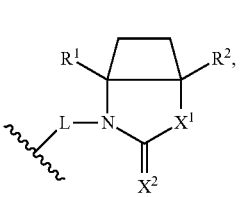

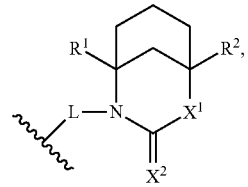 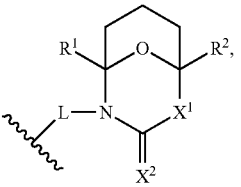

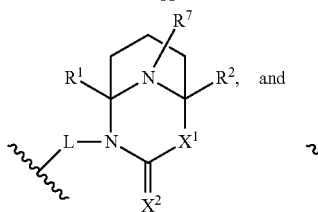

In certain embodiments, $Z^{1'}$, $Z^{2'}$, and $Z^{3'}$ are each null, optionally in combination with one or more of $R^{1'}$, $R^{2'}$ and $R^{3'}$ defined as H, and in other embodiments, both $R^{1'}$ and $R^{2'}$ are H, and in further embodiments, all of $R^{1'}$, $R^{2'}$ and $R^{3'}$ are H, e.g., a compound having one of the following formula:

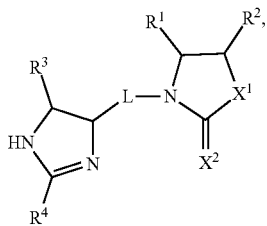

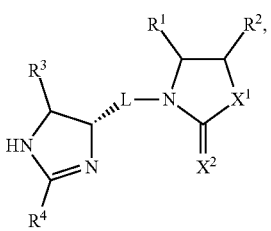

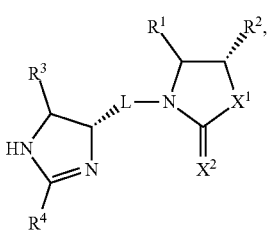

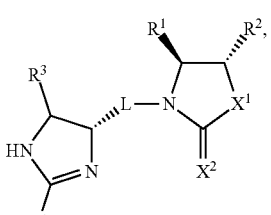

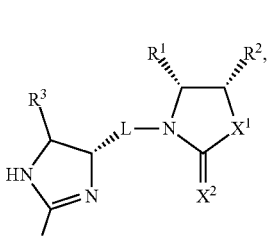

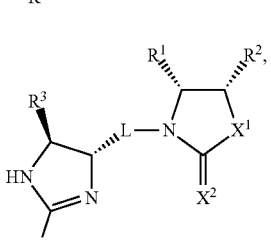

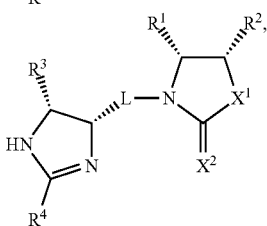

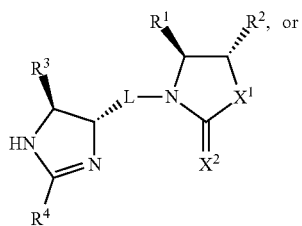
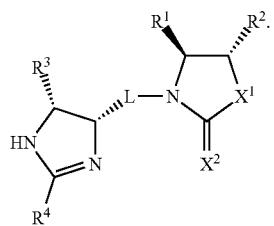
In certain embodiment, $Z^{1'}$, $Z^{2'}$, $Z^3$, and $Z^{3'}$ are each null. In exemplary embodiments, $R^{1'}$, $R^{2'}$, $R^3$ and $R^{3'}$ are each H, e.g., a compound having the formula:
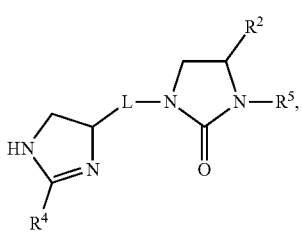
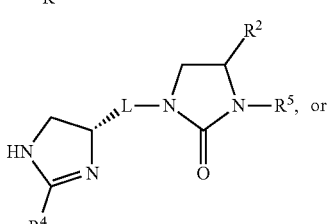
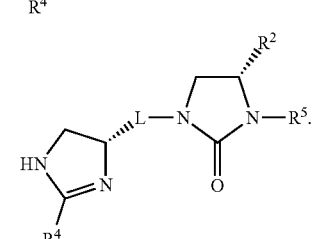
Exemplary embodiments include compounds having the formula:
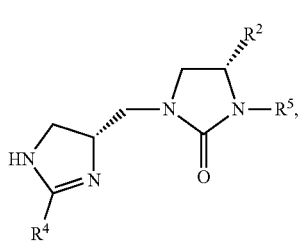
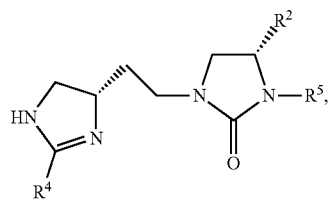
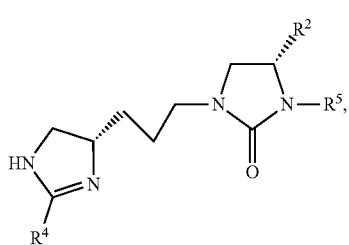
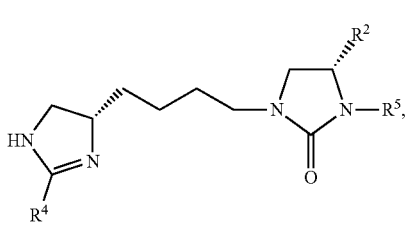
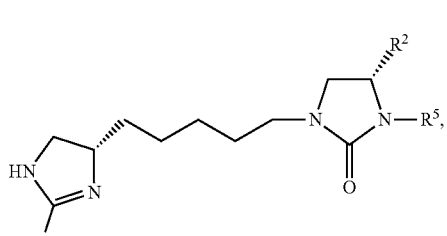
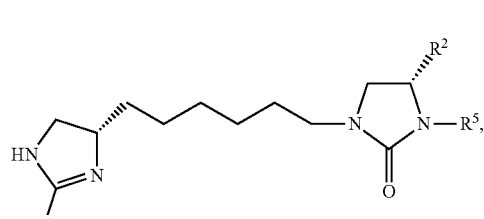
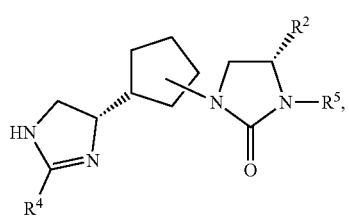
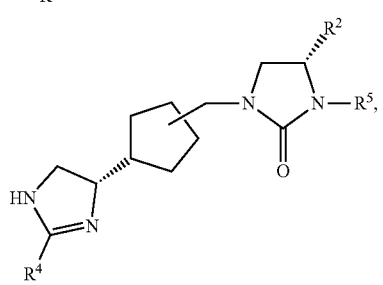

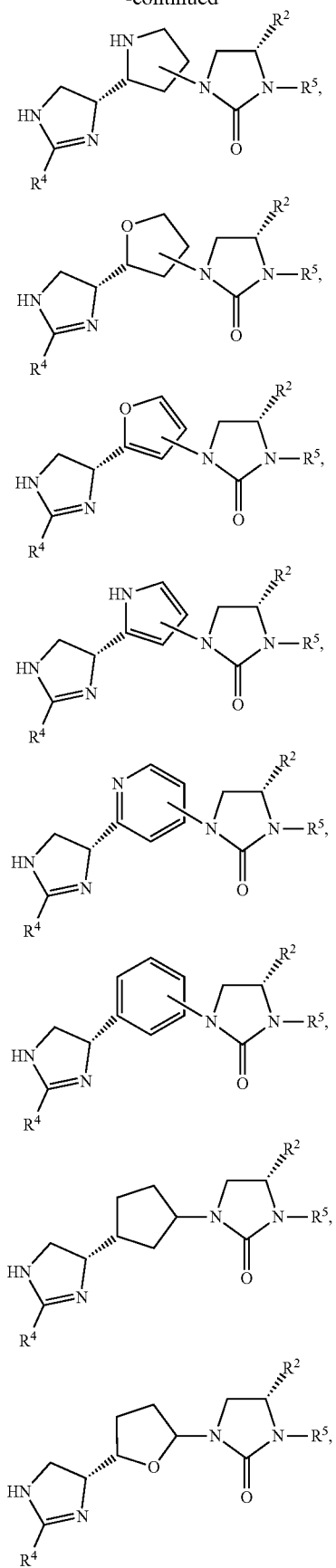

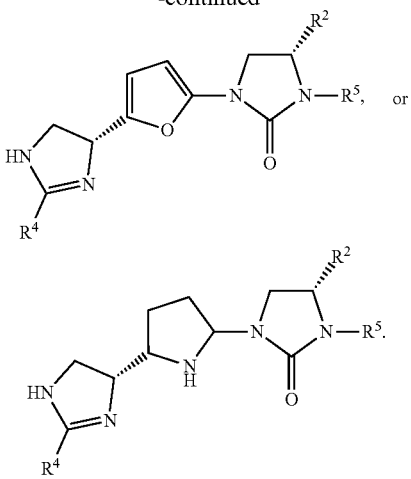

In some instances, $R^2$ is $Z^2$—$R^{2a}$; wherein $Z^2$ is a null, methylene, or ethylene, and $R^{2a}$ is an aryl or heteroaryl group. Suitable aryl groups include phenyls and naphthyls.

In some embodiments, $R^{2a}$ is an aryl group having the formula:

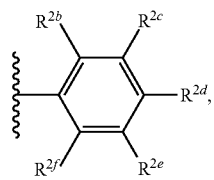

wherein $R^{2b}$ is selected from H, $C_{1-6}$alkyl, $C_{1-6}$haloalkyl, OH, $C_{1-6}$alkyl-OH, $OC_{1-6}$alkyl, $OC_{1-6}$alkyl-OH, $NH_2$, $NHC_{1-6}$alkyl, or $N(C_{1-6}alkyl)_2$;

wherein $R^{2c}$ is selected from H, $C_{1-6}$alkyl, $C_{1-6}$haloalkyl, OH, $C_{1-6}$alkyl-OH, $OC_{1-6}$alkyl, $OC_{1-6}$alkyl-OH, $NH_2$, $NHC_{1-6}$alkyl, or $N(C_{1-6}alkyl)_2$;

wherein $R^{2d}$ is selected from H, $C_{1-6}$alkyl, $C_{1-6}$haloalkyl, OH, $C_{1-6}$alkyl-OH, $OC_{1-6}$alkyl, $OC_{1-6}$alkyl-OH, $NH_2$, $NHC_{1-6}$alkyl, or or $N(C_{1-6}alkyl)_2$;

wherein $R^{2e}$ is selected from H, $C_{1-6}$alkyl, $C_{1-6}$haloalkyl, OH, $C_{1-6}$alkyl-OH, $OC_{1-6}$alkyl, $OC_{1-6}$alkyl-OH, $NH_2$, $NHC_{1-6}$alkyl, or $N(C_{1-6}alkyl)_2$;

wherein $R^{2f}$ is selected from H, $C_{1-6}$alkyl, $C_{1-6}$haloalkyl, OH, $C_{1-6}$alkyl-OH, $OC_{1-6}$alkyl, $OC_{1-6}$alkyl-OH, $NH_2$, $NHC_{1-6}$alkyl, or $N(C_{1-6}alkyl)_2$; and wherein any two or more of $R^{2b}$, $R^{2c}$, $R^{2d}$, $R^{2e}$, and $R^{2f}$ may together form a ring.

By way of example, $R^{2b}$ and $R^{2c}$ can each be $OC_{1-6}$alkyl or $OC_{1-6}$alkyl, and can together form a ring, e.g:

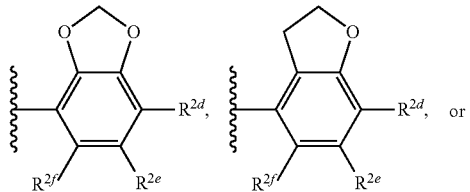

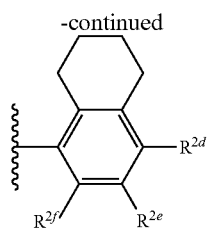

In certain preferred embodiments,
$R^{2b}$ is selected from H, $C_{1-6}$alkyl, OH, $C_{1-6}$alkyl-OH, $OC_{1-6}$alkyl, or $OC_{1-6}$alkyl-OH;
$R^{2c}$ is selected from H, $C_{1-6}$alkyl, OH, $C_{1-6}$alkyl-OH, $OC_{1-6}$alkyl, or $OC_{1-6}$alkyl-OH;
$R^{2d}$ is selected from H, $C_{1-6}$alkyl, OH, $C_{1-6}$alkyl-OH, $OC_{1-6}$alkyl, or $OC_{1-6}$alkyl-OH;
$R^{2e}$ is selected from H, $C_{1-6}$alkyl, OH, $C_{1-6}$alkyl-OH, $OC_{1-6}$alkyl, or $OC_{1-6}$alkyl-OH;
$R^{2f}$ is selected from H, $C_{1-6}$alkyl, OH, $C_{1-6}$alkyl-OH, $OC_{1-6}$alkyl, or $OC_{1-6}$alkyl-OH; and
wherein any two or more of $R^{2b}$, $R^{2c}$, $R^{2d}$, $R^{2e}$, and $R^{2f}$ may together form a ring.

In certain embodiments, both $R^{2b}$ and $R^{2f}$ are H, and $R^{2c}$, $R^{2d}$, and $R^{2e}$ are each independently selected from H, OH, $C_{1-6}$alkyl-OH, and $OC_{1-6}$alkyl; wherein any two or more of $R^{2c}$, $R^{2d}$, and $R^{2e}$ may together form a ring. In some embodiments, $R^{2c}$ and $R^{2e}$ are each H, and $R^{2d}$ is $CH_2OH$ or OH.

In some embodiments, $X^1$ is $NR^5$. Exemplary $R^5$ groups include $C_{1-8}$alk-$C_{3-10}$cycloalkyl, $C_{1-8}$alk-aryl, $C_{1-6}$heterocyclyl, $C_{1-8}$alk-heteroaryl, or $C_{1-8}$alk-$C_{1-6}$heterocyclyl, preferably $C_{1-8}$alk-$C_{3-10}$cycloalkyl or $C_{1-8}$alk-aryl, even more preferably $C_{4-8}$alk-$C_{3-10}$cycloalkyl or $C_{4-8}$alk-aryl. Suitable $C_{3-10}$cycloalkyl groups include cyclohexyl, cycloheptyl, cyclooctyl, norbornanyl, bicyclo[2.2.2]octyl, and adamantyl. In some embodiments the cycloalkyl is unsubstituted, while in other embodiments the cycloalkyl is substituted one or more times by a halogen, especially fluorine. In certain embodiments, the cycloalkyl contains 1, 2, 3, 4, 5, or 6 fluoro substituents.

In some embodiments, $R^5$ can be $C_4$alk-$C_{3-10}$cycloalkyl, $C_4$alk-aryl, $C_{1-6}$heterocyclyl, $C_4$alk-heteroaryl, or $C_4C_{1-6}$heterocyclyl. When $R^5$ includes a cycloalkyl group, suitable $C_{3-10}$cycloalkyl groups include cyclohexyl, cycloheptyl, cyclooctyl, norbornanyl, bicyclo[2.2.2]octyl, and adamantyl.

In some instances, $R^4$ is $Z^4$—$R^{4a}$; and $Z^4$ is a bond, methylene, or ethylene, and $R^{4a}$ is aryl or heteroaryl. For example, $R^{4a}$ can be an aryl group having the formula:

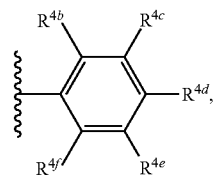

wherein $R^{4b}$ is selected from H, $C_{1-6}$alkyl, OH, $OC_{1-6}$alkyl, $NH_2$, $NHC_{1-6}$alkyl, or $N(C_{1-6}$alkyl$)_2$;
wherein $R^{4c}$ is selected from H, $C_{1-6}$alkyl, OH, $OC_{1-6}$alkyl, $NH_2$, $NHC_{1-6}$alkyl, or $N(C_{1-6}$alkyl$)_2$;
wherein $R^{4d}$ is selected from H, $C_{1-6}$alkyl, OH, $OC_{1-6}$alkyl, $NH_2$, $NHC_{1-6}$alkyl, or $N(C_{1-6}$alkyl$)_2$;
wherein $R^{4e}$ is selected from H, $C_{1-6}$alkyl, OH, $OC_{1-6}$alkyl, $NH_2$, $NHC_{1-6}$alkyl, or $N(C_{1-6}$alkyl$)_2$;
wherein $R^{4f}$ is selected from H, $C_{1-6}$alkyl, OH, $OC_{1-6}$alkyl, $NH_2$, $NHC_{1-6}$alkyl, or $N(C_{1-6}$alkyl$)_2$; and
wherein any two or more of $R^{4b}$, $R^{4c}$, $R^{4d}$, $R^{4e}$, and $R^{4f}$ may together form a ring.

In certain embodiments,
$R^{4b}$ is selected from H, $C_{1-6}$alkyl, OH, or $OC_{1-6}$alkyl;
$R^{4c}$ is selected from H, $C_{1-6}$alkyl, OH, or $OC_{1-6}$alkyl;
$R^{4d}$ is selected from H, $C_{1-6}$alkyl, OH, or $OC_{1-6}$alkyl;
$R^{4e}$ is selected from H, $C_{1-6}$alkyl, OH, or $OC_{1-6}$alkyl;
wherein $R^{4f}$ is selected from H, $C_{1-6}$alkyl, OH, or $OC_{1-6}$alkyl; and
wherein any two or more of $R^{4b}$, $R^{4c}$, $R^{4d}$, $R^{4e}$, and $R^{4f}$ may together form a ring.

In some instances, $R^{4b}$ and $R^{4f}$ are each H, and $R^{4c}$, $R^{4d}$, and $R^{4e}$ are each independently selected from H, OH, and $OC_{1-6}$alkyl; wherein any two or more of $R^{4c}$, $R^{4d}$, and $R^{4e}$ may together form a ring. In further embodiments, $R^{4c}$ and $R^{4e}$ are each H, and $R^{4d}$ is OH, $OCH_3$, or $OCH_2CH_3$.

Figure 11:
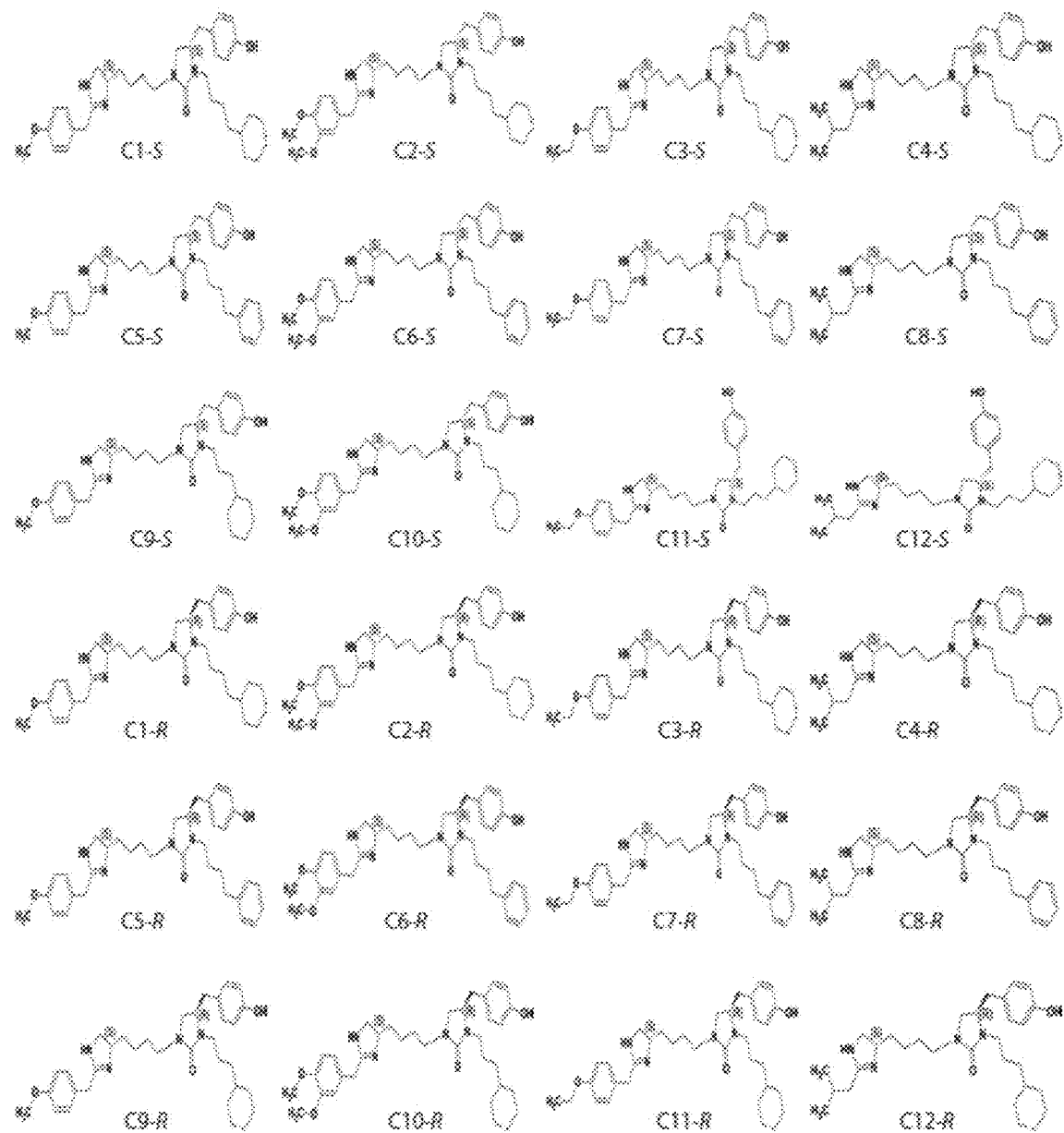
FIG. 11 depicts the chemical structure of certain compounds of the invention.
Figure 12:
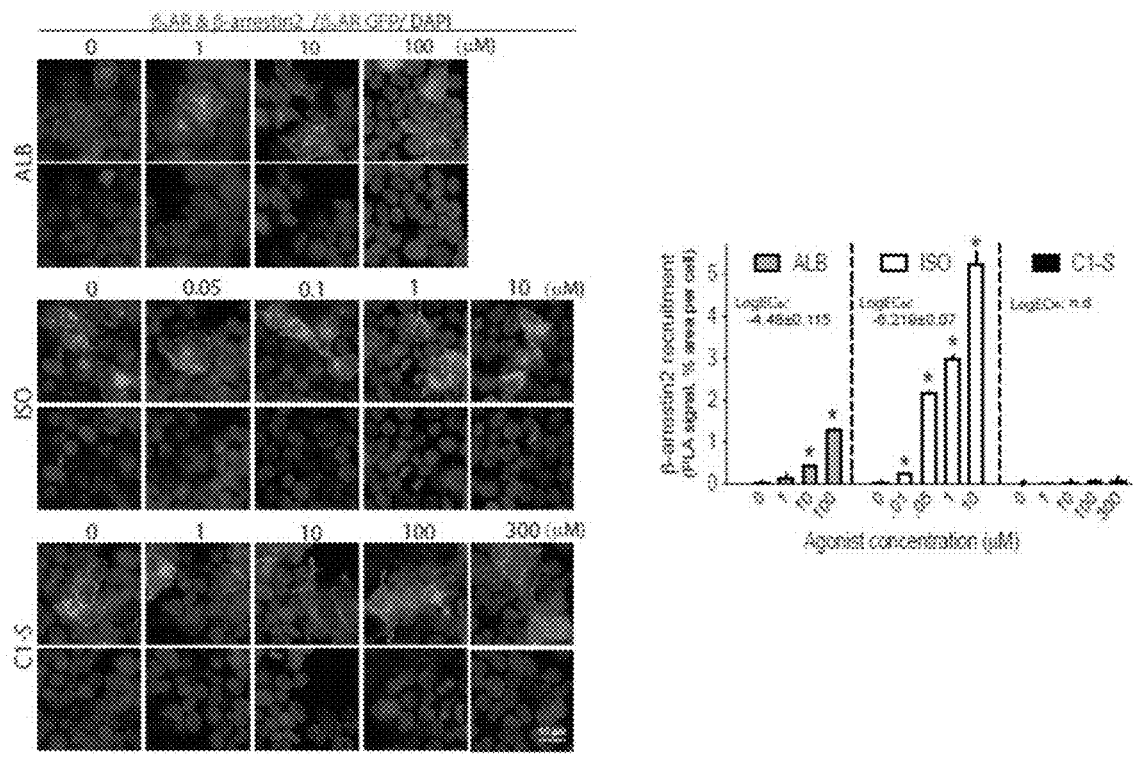
FIG. 12 depicts that C1-S fails to promote $β_2AR$ binding to β-arrestin as determined by a PLA. Transfected cells were exposed to the agonists albuterol (ALB), isoproterenol (ISO), and C1-S at the indicated concentrations for 10 minutes. 4 experiment were performed and visualized by confocal microscopy. The red signal indicates β-arrestin binding to the receptor. The mean±SE of the maximal response the $EC_{50}$ indicated for each agonist is also depicted. There was no β-arrestin response from C1-S, so the $EC_{50}$ was not determined (n.d.) *P<0.01 vs. vehicle control.
Figure 13:
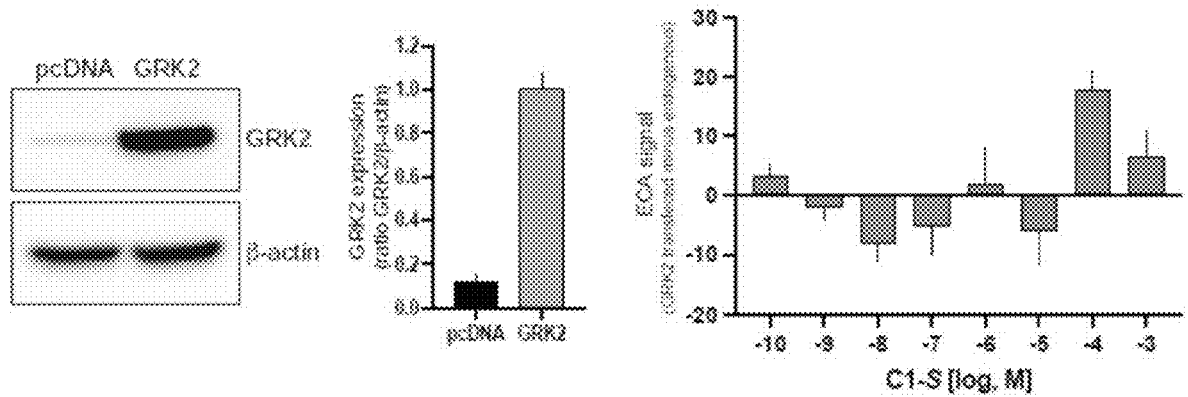
FIG. 13 depicts GRK2 overexpression does not increase C1-S promoted β-arrestin binding to $β_2AR$ as determined by the ECA. Stably infected CHO cells expressing modified $β_2AR$ and β-arrestin were transiently transfected with GRK2 to achieve >8 fold overexpression compared to endogenous GRK2. Parallel ECAs performed with or without GRK2 overexpression using the indicated concentrations of C1-S. The differences in the ECA signal between cells overexpressing and endogenously expressing GRK2 were determined at each concentration (set as the y-axis). These differences fluctuated and included both positive and negative values, and ANOVA failed to show significance. Results are from 4-6 experiments.
Figure 14A:
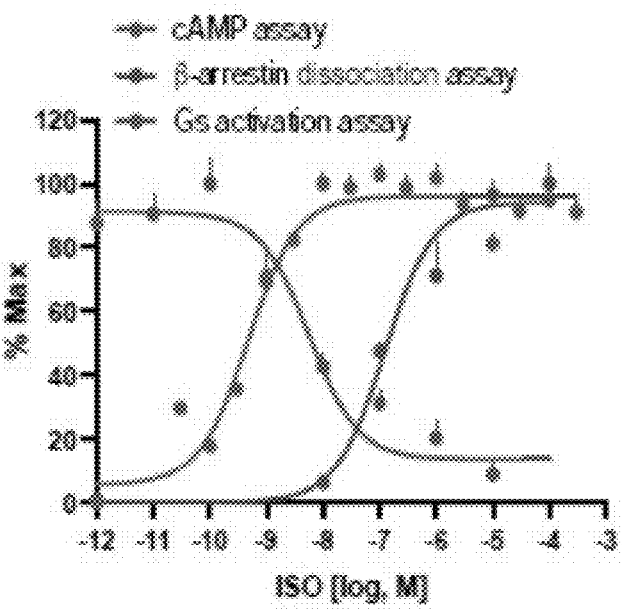
FIG. 14A depicts dose-responses of cAMP stimulation, β-arrestin binding, and Gs activation with isoproterenol (ISO).
Figure 14B:
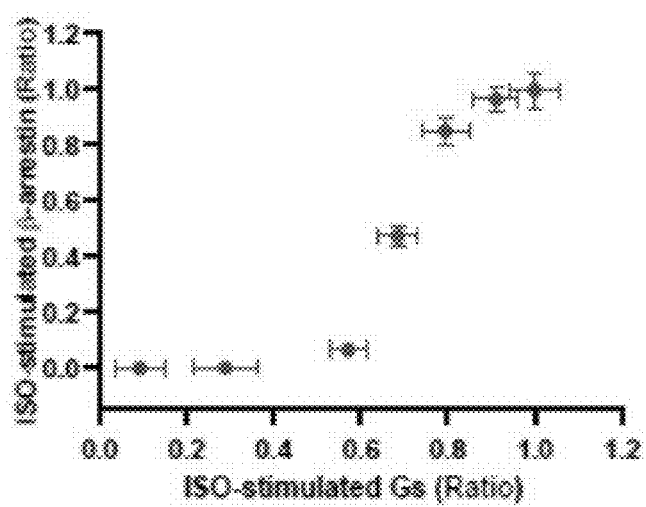
FIG. 14B depicts a bias plot constructed using data from the Gs-activation and the β-arrestin binding assays, indicating "space" where biasing in either direction by a compound could be detected.
Figure 14C:
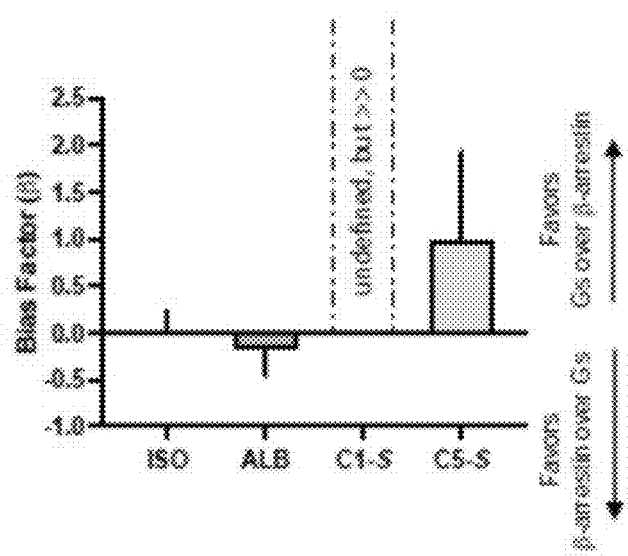
FIG. 14C depicts the calculated bias factors indexed to ISO. Albuterol (ALB) and C5-S factors were not statistically different that 0. The C1-S value is not defined since no β-arrestin binding was detected, but R is considered positive since the agonist activates Gs, stimulates cAMP, and relaxes HASM.
Figure 15:
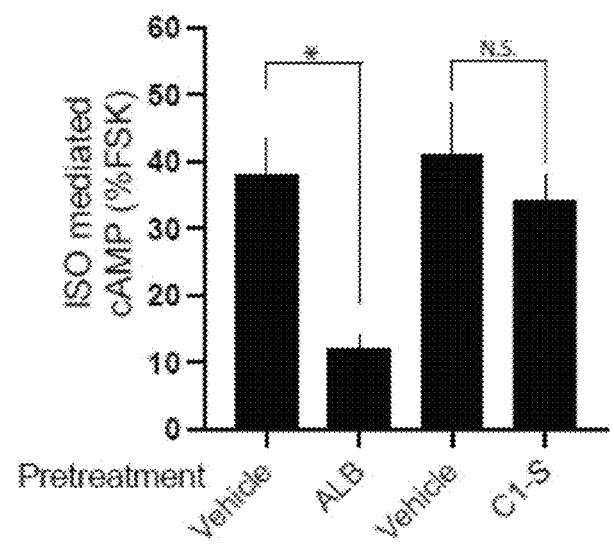
FIG. 15 depicts that C1-S does not promote short-term agonist mediated desensitization of $\beta_2$AR. Attached CHO-$\beta_2$ cells were exposed to vehicle, 10 μM albuterol (ALB) or 150 μM C1-S for 10 minutes, washed, and the cAMP response to 10 μm isoproterenol (ISO) determined after a 10 minute incubation. ALB pretreatment resulted in ~68% desensitization of the subsequent ISO response. In contrast, C1-S pretreatment caused no desensitization. *, P<0.01 vs vehicle, N=4 experiments.
Figure 16:
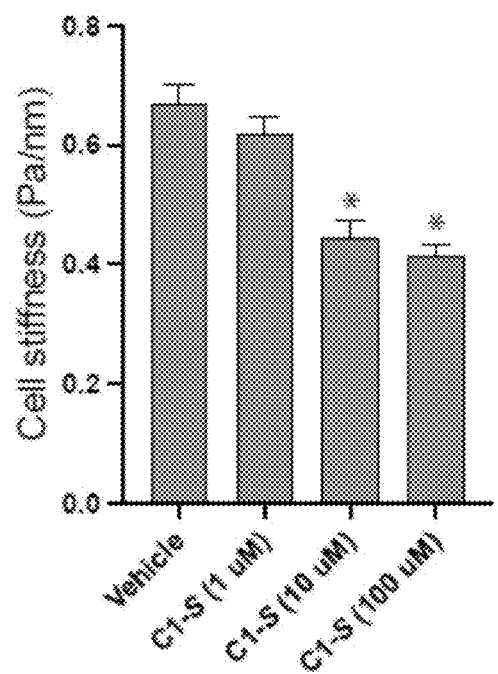
FIG. 16 depicts that C1-S relaxes human airway smooth muscle cells. MTC was utilized to measure cell stiffness (shown as raw values), where a decrease in stiffness represents relaxation. The maximal response at the three indicated concentrations are shown. *, P<0.01 vs vehicle, N=4 experiments.
Figure 17:
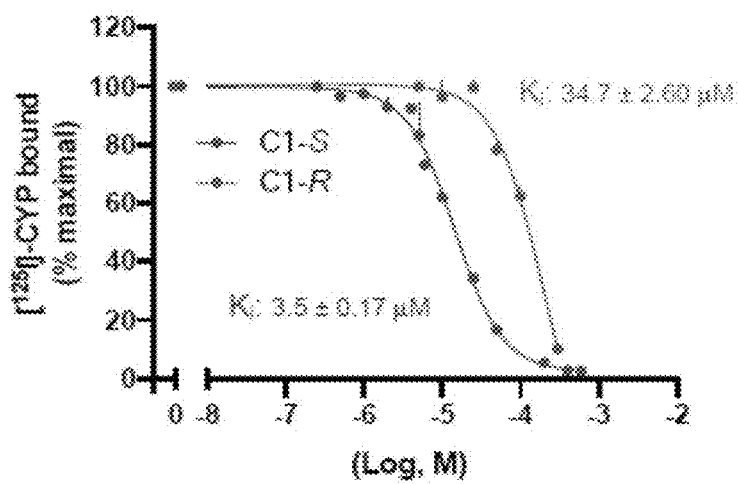
FIG. 17 depicts the competition between C1-S or C1-R with the PAR radioligand $^{125}$ICYP for $\beta_2$AR expressed on cell membranes. The stable CHW-$\beta_2$ cell line was used to prepare cell membranes and competition studies were performed with 60 pM $^{125}$ICYP in the presence of 100 μm GTP. Results are from three experiments.
Figure 18A:
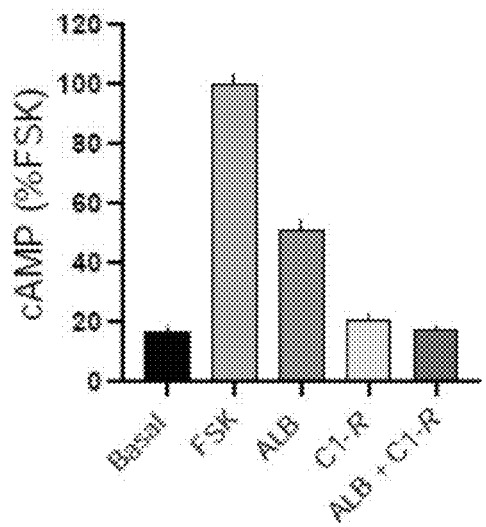
FIG. 18A depicts intact CHW-$\beta_2$ were exposed for 10 minutes to vehicle (basal), 5 μM forskolin (FSK), 10 nM alburterl (ALB), or 10 nM albuterol+300 μM C1-R, and cAMP levels determined. There was no difference between basal and ALB_C1-R cAMP levels.
Figure 18B:
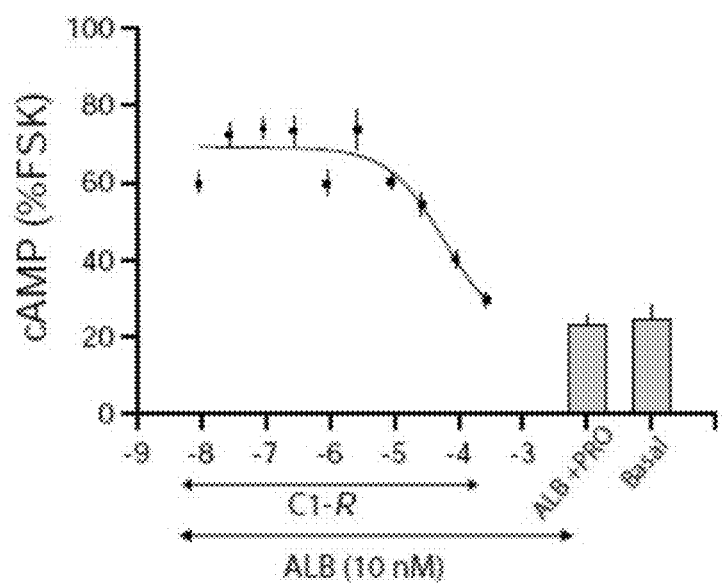
FIG. 18B depicts dose-response of C1-R for antagonizing ALB-promoted cAMP. Propranolol (PRO, 1.0 μM), served as a known antagonist. N=3-4 experiments.

Exemplary compounds include those depicted in FIG. 11, and compounds having the formula:

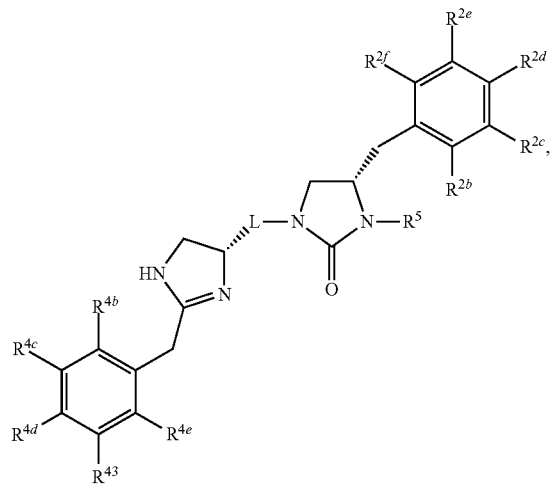

In some embodiments the compound may have the formula:

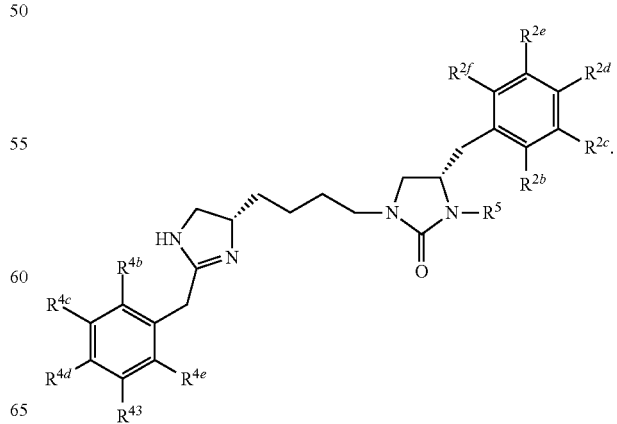

In further embodiments, the compound can have the formula:

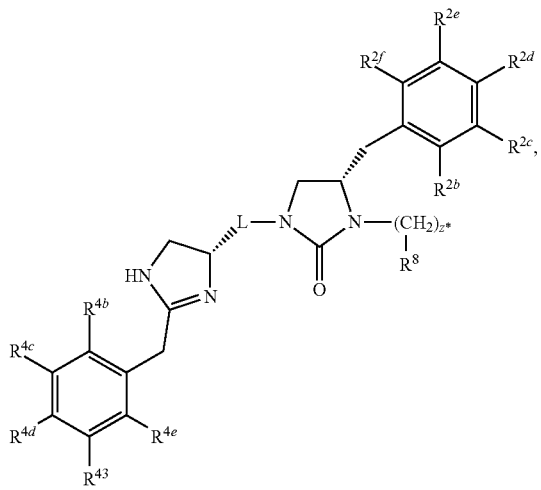

wherein z* is 1, 2, 3, 4, 5, or 6, and $R^8$ is $C_{3-10}$cycloalkyl, for example cyclohexyl, cycloheptyl, cyclooctyl, norbornanyl, bicyclo[2.2.2]octyl, or adamantyl.

Disclosed are methods of treating an obstructive lung disease or condition in a subject, comprising administering a therapeutically effective amount of a pharmaceutical composition comprising one or more compounds disclosed herein to a subject in need of treatment. In particular aspects, the obstructive lung disease or condition can be, e.g., asthma, chronic obstructive pulmonary disease (COPD), emphysema or bronchitis.

In a second aspect, provided herein are methods of inducing bronchodilation in a subject, comprising administering a therapeutically effective amount of a pharmaceutical composition comprising one or more compounds disclosed herein to a subject in need of bronchodilation.

In a third aspect, provided herein are methods of relaxing airway smooth muscle (ASM) in a subject, comprising administering a therapeutically effective amount of a pharmaceutical composition comprising one or more compounds disclosed herein to a subject in need of ASM relaxation.

In a fourth aspect, provided herein are methods of treating or preventing bronchoconstriction or bronchospasm in a subject, comprising administering a therapeutically effective amount of a pharmaceutical composition comprising one or more compounds disclosed herein to a subject in need of treatment or prevention of bronchoconstriction or bronchospasm.

The obstructive lung diseases and conditions encompassed by the present invention include any respiratory condition or disease, whether acute or chronic, characterized by impairment of airflow into and/or out of the lungs of a subject. Obstructive lung diseases and conditions include, e.g., asthma, chronic obstructive pulmonary disease (COPD), emphysema and bronchitis, as well as cystic fibrosis, bronchiectasis, bronchiolitis, and allergic bronchopulmonary aspergillosis. Another such obstructive lung disease or condition that can be treated or prevented by administering compounds as described herein includes bronchoconstriction or bronchospasm that can be caused, e.g., by inhalation of a noxious compound such as smoke or a corrosive chemical; by a respiratory infection; or by anaphylaxis such as that caused by sepsis or an allergic reaction to a food (e.g., peanuts), a drug (e.g., penicillin), an insect sting or bite, pollen, mold, dust mites, latex, or other substances; or by other triggers of bronchoconstriction or bronchospasm. For example, the compounds can be administered to prevent (or treat) bronchospasm induced by exercise or air pollution. In another example, the compounds can be administered before or during placement of a breathing tube to prevent (or treat) bronchospasm induced by placement of the tube. The compounds of the invention can be administered to healthy individuals in situations in which it might be desirable to increase bronchodilation to improve oxygen uptake, e.g., in lower oxygen environments (such as several thousand feet above sea level) or to improve athletic performance.

The pharmaceutical compositions of the present invention comprising one or more compounds disclosed herein may also comprise one or more of a carrier, diluent and excipient (e.g., a pharmaceutically acceptable carrier, diluent, or excipient), depending on the identity of the compound. By "pharmaceutically acceptable" is meant a material that is not biologically or otherwise undesirable, i.e., the material may be administered to an individual along with the compound without causing any undesirable biological effects or interacting in a deleterious manner with any of the components of the pharmaceutical composition in which it is contained. Conventional pharmaceutical practice may be employed to provide suitable formulations or compositions to administer such compositions to subjects. The terms specifically exclude cell culture medium. Suitable diluents (for both dry and liquid pharmaceutical formulations) are well known to those skilled in the art and include saline, buffered saline, dextrose (e.g., 5% dextrose in water), water, glycerol, ethanol, propylene glycol, polysorbate 80 (Tween-80™) poly (ethylene)glycol 300 and 400 (PEG 300 and 400), PEGylated castor oil (e.g. Cremophor EL), poloxamer 407 and 188, a cyclodextrin or a cyclodextrin derivative (including HPCD ((2-hydroxypropyl)-cyclodextrin) and (2-hydroxyethyl)-cyclodextrin; see, e.g., U.S. patent application publication 20060194717).

Carriers are compounds and substances that improve and/or prolong the delivery of an active ingredient to a subject in the context of a pharmaceutical formulation. Carriers may serve to prolong the in vivo activity of a drug or slow the release of the drug in a subject, using controlled-release technologies. Carriers may also decrease drug metabolism in a subject and/or reduce the toxicity of the drug. Carriers can also be used to target the delivery of the drug to particular cells or tissues in a subject. Common carriers (both hydrophilic and hydrophobic carriers) include fat emulsions, lipids, PEGylated phospholids, liposomes and lipospheres, microspheres (including those made of biodegradable polymers or albumin), polymer matrices, biocompatible polymers, protein-DNA complexes, protein conjugates, erythrocytes, vesicles and particles.

Excipients included in a pharmaceutical composition have different purposes depending, for example on the nature of the drug, and the mode of administration. Examples of generally used excipients include, without limitation: stabilizing agents, solubilizing agents and surfactants, buffers and preservatives, tonicity agents, bulking agents, lubricating agents (such as talc or silica, and fats, such as vegetable stearin, magnesium stearate or stearic acid), emulsifiers, suspending or viscosity agents, inert diluents, fillers (such as cellulose, dibasic calcium phosphate, vegetable fats and oils, lactose, sucrose, glucose, mannitol, sorbitol, calcium carbonate, and magnesium stearate), disintegrating agents (such as crosslinked polyvinyl pyrrolidone, sodium starch glycolate, cross-linked sodium carboxymethyl cellulose), binding agents (such as starches, gelatin, cellulose, methyl cellulose or modified cellulose such as microcrystalline cellulose, hydroxypropyl cellulose, sugars such as sucrose and lactose, or sugar alcohols such as xylitol, sorbitol or maltitol, polyvinylpyrrolidone and polyethylene glycol), wetting agents, antibacterials, chelating agents, coatings (such as a cellulose film coating, synthetic polymers, shellac, corn protein zein or other polysaccharides, and gelatin), preservatives (including vitamin A, vitamin E, vitamin C, retinyl palmitate, and selenium, cysteine, methionine, citric acid and sodium citrate, and synthetic preservatives, including methyl paraben and propyl paraben), sweeteners, perfuming agents, flavoring agents, coloring agents, administration aids, and combinations thereof.

The pharmaceutical compositions of the present invention can be formulated for pulmonary administration, whether for nasal or buccal inhalation. The unit dosage of the pharmaceutical composition may be conveniently delivered in the form of an aerosol spray from a pressurized pack or a nebulizer, or via a vaporizer. The pharmaceutical compositions may also be delivered as a formulated powder and the powder composition may be inhaled with the aid of an insufflation powder inhaler device. One example of a delivery system for inhalation is a metered dose inhalation (MDI) aerosol, which may be formulated as a dry suspension or wet solution of a pharmaceutical composition of the invention in a suitable propellant, such as a fluorocarbon solvent or a hydrocarbon solvent. Suitable fluorocarbon solvents include HFA-134a (1,1,1,2-tetrafluoroethane), HFA-227ea (1,1,1,2,3,3,3-heptafluoropropane), HFA-152a (1,1-difluoroethane) and combinations thereof. For propellant formulations, the propellant may be present in an amount that is at least 5% by weight, at least 10% by weight, at least 25% by weight, at least 50% by weight at least 75% by weight, or at least 90% by weight, relative to the entire formulation. In some embodiments, the propellant is present in an amount from 80-99.9% by weight, or from 90-99.9% by weight, relative to the entire formulation. The propellant formulation may also include one or more stabilizing excipients, such as ethanol and oleic acid. When ethanol is used, it may be present in an amount from 0.5-10% by weight, from 1-5% by weight, or from 5-10% by weight, relative to the entire formulation. The propellant formulations may further include one or more surfactants, for instance in an amount from 0.1-2.5% by weight, or from 0.2-1.5% by weight, relative to the entire formulation.

The compounds may be in particulate form to enhance delivery to the lung. For example, the compounds may be provided with a particle from 0.1-10 μm, from 0.1-5 μm, from 0.5-2.5 μm, from 1-5 μm, from 2.5-5 μm, or from 1-2.5 μm. In the case of dry powder formulations, the disclosed compounds may be provided in an amount from 1-50% by weight, from 1-50% by weight, from 5-50% by weight, from 1-25% by weight, from 10-25% by weight, from 15-50% by weight, or from 25-50% by weight relative to the total weight of the formulation. The dry powder formulations may further include a powdered matrix material, for example a polyol or carbohydrate, e.g., sorbitol, mannitol, xylitol, glucose, arabinose, lactose, maltose, saccharose, dextrose and mixtures thereof. The compositions may further include a surfactant, for example in an amount from 0.1-10% by weight, from 0.1-5% by weight, 1-10% by weight, from 1-5% by weight, 2.5-10% by weight, or from 2.5-5% by weight. Suitable surfactants include lecithin, phospholipids derivatives such as phosphatic acids, phosphatidyl choline (saturated and unsaturated), phosphatidyl ethanol amine, phosphatidyl glycerol, phosphatidyl serine, phosphatidyl inositol, dioleoylphosphatidylcholine, dimyristoyl phosphatidylcholine, dipalmitoylphosphatidylcholine, distearoyl phosphatidylcholine, diarachidoyl phosphatidylcholine, dibenoyl phosphatidylcholine, ditricosanoyl phosphatidylcholine, dilignoceroylphatidylcholine, dimiristoylphosphatidylethanol-amine, dipalmitoyl-phosphatidylethanoalamine, pipalmitoleoylphasphatidylethanolamine, distearoyl-phosphatidylethanolamine, dimyristoylphosphatidylglycerol, dipalmitoylphosphatidyl glycerol, dipalmitolcoylphosphatidylglycerol, and mixtures thereof.

In addition, any other appropriate route for administration can be employed, for example, but not limited to, intravenous, parenteral, transbuccal, transdermal, transcutaneous, subcutaneous, intranasal, aerosol, or oral administration. Therapeutic formulations may be in the form of liquid solutions or suspensions; for example, for oral administration, formulations may be in the form of tablets or capsules; for intranasal formulations, in the form of powders, nasal drops, or aerosols; for transdermal formulations, in the form of creams or distributed onto patches to be applied to the skin.

Effective amounts of the one compounds disclosed herein in a pharmaceutical formulation will vary depending on the compound being used and the condition or disease being treated, as well as factors such as age of the subject and other medications being taken. Effective dosages will typically be set by an attending physician as is well known in the art. However, the concentration of the compounds delivered to a subject in a unit dose will generally range from about 0.05 mg to about 100 mg, or a value within this range. The combinations can be administered in combinations and/or in combination with one or more other agent (e.g. but not limited to a beta-agonist such as albuterol). In one non-limiting example provided herein, the compounds can be administered with either isoproterenol or chloroquine is additive; thus, under some circumstances, it can be appropriate to administer either (or both) of these agents combination with the compounds disclosed herein to a subject in need thereof.

As used herein, the terms "dose", "dosage", "unit dose", "unit dosage", "effective dose" and related terms refer to physically discrete units that contain a predetermined quantity of active ingredient calculated to produce a desired therapeutic effect (e.g., bronchodilation or relaxation of the airways). These terms are synonymous with the therapeutically effective amounts and amounts sufficient to achieve the stated goals of the methods disclosed herein.

As used herein, the terms "treat", "treating", and "treatment" have their ordinary and customary meanings, and include one or more of, ameliorating a symptom of an obstructive lung disease or condition in a subject, blocking or ameliorating a recurrence of a symptom of an obstructive lung disease or condition in a subject, decreasing in severity and/or frequency a symptom of an obstructive lung disease or condition in a subject. As used herein, "treatment" includes at least partially, and at least temporarily, relieving bronchoconstriction (or bronchospasm) or increasing bronchodilation, so that the patient or subject can breathe more easily. Treatment means ameliorating, blocking, reducing, decreasing or inhibiting by about 1% to about 100% versus a subject to which a pharmaceutical composition has not been administered. Preferably, the ameliorating, blocking, reducing, decreasing or inhibiting is about 100%, 99%, 98%, 97%, 96%, 95%, 90%, 80%, 70%, 60%, 50%, 40%, 30%, 20%, 10%, 5% or 1% versus a subject to which a pharmaceutical composition has not been administered.

As used herein, the terms "prevent", "preventing", and "prevention" have their ordinary and customary meanings, and include one or more of preventing a symptom of an obstructive lung disease or condition in a subject, blocking a recurrence of a symptom of an obstructive lung disease or condition in a subject, and decreasing in frequency a symptom of an obstructive lung disease or condition in a subject. As used herein, "prevention" includes at least partially, and at least temporarily, blocking bronchoconstriction (or bronchospasm) so that breathing is not inhibited in the patient or subject. The prevention may be protection of about 100%, 99%, 98%, 97%, 96%, 95%, 90%, 80%, 70%, 60%, 50%, 40%, 30%, 20%, 10%, 5% or 1% in the subject, versus a subject to which a pharmaceutical composition has not been administered. The prevention lasts at least about 1, 2, 3, 4, 5, 6, 7, 8, 9, 10, 11, 12, 13, 14, 15, 16, 17, 18, 19, 20, 21, 22, 23, or 24, or more, hours after administration of a pharmaceutical composition.

EXAMPLES

The following examples are for the purpose of illustration of the invention only and are not intended to limit the scope of the present invention in any manner whatsoever.

Example 1

CHW cells were transfected to stably express the human $\beta_2$AR under G418 selection and maintained in monolayers as previously described. Transient transfections of HEK-293T cells with constructs to express human β-arrestin2-myc, human β-arrestin2-GFP, human $\beta_2$AR and $\beta_2$AR-GFP, were performed using Lipofectamine 2000 (Invitrogen), and studied 48 hrs later. CHO cells stably expressing a modified $\beta_2$AR and a modified β-arrestin2 for the ECA were purchased from DiscoverX. In some experiments, these cells were transiently transfected with 5 μg GRK2 cDNA. Primary HASM cells were derived from donor lungs obtained from the National Disease Exchange Registry and maintained as monolayers, and utilized between passages 3 and 6 for the physiological studies. Other experiments used the D9 telomerase reverse transcriptase immortalized HASM cell line (D9-HASM).

Individual compounds were synthesized using standard synthetic methods to 95% purity and verified by high pressure liquid chromatography.

For radioligand competition studies, CHW-β2 cell membranes were incubated with $^{125}$ICYP (60 pM) in 75 mM Tris (pH 7.4), 12 mM MgCl$_2$, 2 mM EDTA buffer containing 100 μM GTP and the indicated concentrations of compounds for 1.5 hrs at 25° C. Bound $^{125}$ICYP was separated from free radioligand by filtration over glass fiber filters with 5 mM Tris (pH 7.4), 2 mM EDTA buffer at 4° C. using a cell harvester (Brandell). Filters were counted in a gamma counter at 70% efficiency. For cAMP experiments, $\beta_2$AR-transfected and nontransfected cells were plated onto 96 well plates at 20,000 cells per well in Dulbecco's modified Eagle's media (DMEM) without serum, and the next day treated with the phosphodiesterase inhibitor 3-isobutyl-1-methylzanthine (100 μM for 30 min). cAMP production from the cells was initiated by exposure to various agents for 10 min at 37° C., and the reaction stopped by cell lysis. Wells received DMF (0.25%, the carrier, representing basal cAMP levels), 10 μM forskolin, aliquots from the multidrug screening sample wells from the libraries (stock=250 μg/ml), or various concentrations of individual compounds as indicated. Assays were performed in duplicate. cAMP was measured by a competitive immunoassay (Molecular Devices with readings taken by a FlexStation3 automated plate reader (Molecular Devices). ERK1/2 activation was determined in HASM cells by treating cells for 5 min at 37° C. with vehicle, 10 μM isoproterenol, 100 μM albuterol, or 100 μM C1-S, and the proteins separated by 12% SDS-gel electrophoresis and transferred with the following antibodies: phosho-ERK1/2 (1:1000 titer, Cell Signaling), total ERK1/2 (1:1000 titer, Cell Signaling), and secondary antibody (1:10000 titer, Amersham Biosciences). Blots were developed by enhanced chemiluminescence, imaged on a ChemiDoc MP (BioRad), and quantitated using ImageJ software (National Institutes of Health).

HEK-293T cells were transfected on coverslips with $\beta_2$AR-GFP and β-arrestin2-myc. Primary antibodies to each tag are incubated with transfected cells and then a pair of oligo-coupled secondary antibodies are added to the dish. Hybridizing oligos connect the two antibody-coupled oligos when they are in close proximity. A signal is generated after a ligase forms circular DNA, which is then amplified by rolling-circle PCR. Fluorescent-labeled oligos hybridize to this product. Cells were exposed to vehicle, or the indicated concentrations of agonists for 10 min at 37° C., and fixed with 4% paraformaldehyde. Cells were imaged by fluorescence confocal microscopy (40× magnification, 4× zoom) with 594 nm excitation and 624 nm emission wavelengths to acquire the red spectra (the PLA signal) and 489 nm excitation and 510 nm emission wavelengths to visualize the receptor-GFP signal. The data was analyzed by ImageJ software. The ECA (PathHunter, DiscoverX) was performed as an additional approach to detect receptor β-arrestin interaction. Briefly, attached CHO cells, stably transfected to express a β-arrestin2 fused to a β-galactosidase that lacks a peptide fragment, and a $\beta_2$AR that is tagged at its C-terminus with the complementation β-galactosidase fragment, were studied in 96 well plates. Agonists were incubated for 30 min at 37° C. Upon agonist-promoted binding of β-arrestin to receptor, the β-galactosidase is reconstituted to yield active enzyme which is detected by luminescence on a FlexStation3 plate reader. The β-arrestin-GFP based recruitment assays were performed as previously described (15). HEK-293T cells were transiently transfected on coverslips with constructs encoding β-arrestin2-GFP and $\beta_2$AR as indicated above. 48 hours after transfection, cells were treated with vehicle, the indicated concentrations of agonist, and the confocal images captured in real time over the next 20 min.

Gαs activation by $\beta_2$AR was quantitated by determining the dissociation of the Gs heterotrimer using BRET2. HEK293T cells were transfected using Lipofectamine 2000 with cDNA constructs encoding $\beta_2$AR, the short form of Gαs fused to RLuc8, Gb, and Gg fused to GFP2 (Addgene) at a ratio of 1:1:1:1. The next day they were lifted and plated on 96 well plates, and 48 hrs after transfection the RLuc8 substrate was added and cells were treated with multiple doses of agonist in quadruplicate for 5 min at room temperature. The Rluc8 signal was acquired at 395 nm and the GFP2 signal at 510 nm on a FlexStaion3. BRET2 was calculated as the ratio of the GFP2 to RLuc8 signals. Agonist-promoted dissociation of the G-protein heterodimer results in a decrease in the BRET2 signal as the energy donor and energy acceptor are distanced.

Figure 6A:
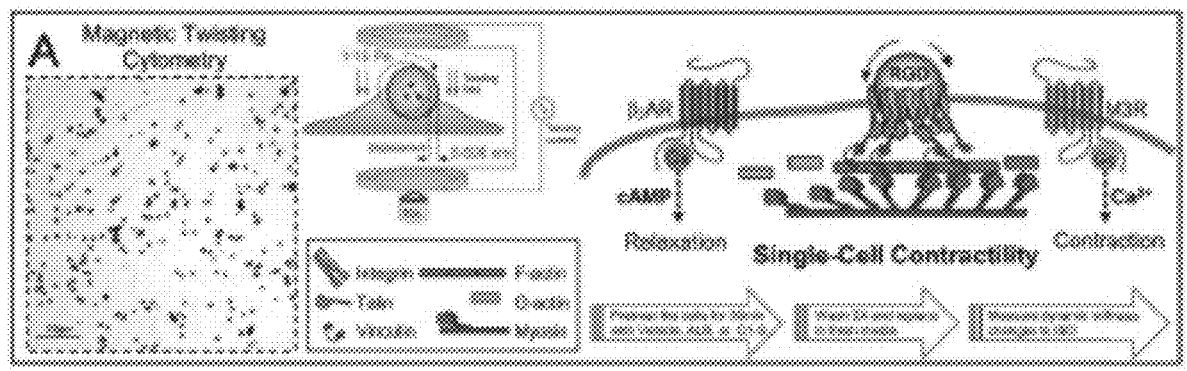
FIG. 6A depicts the agonist C1-S fails to evoke desensitization of HASM $β_2AR$-mediated relaxation. Single cell mechanics of HASM cells were studied using magnetic twisting cytometry. RGD-coated ferrimagnetic microbeads were attached to integrin receptors. Cells were magnetized horizontally, and then twisted in a vertically aligned magnetic field. A decrease in the twisting force was quantified by lateral bead displacement in response to the application of various bAR agonists added to the media. A decrease in stiffness correlates with airway smooth muscle cell relaxation. The desensitization protocol is shown by the large arrows.
Figure 6B:
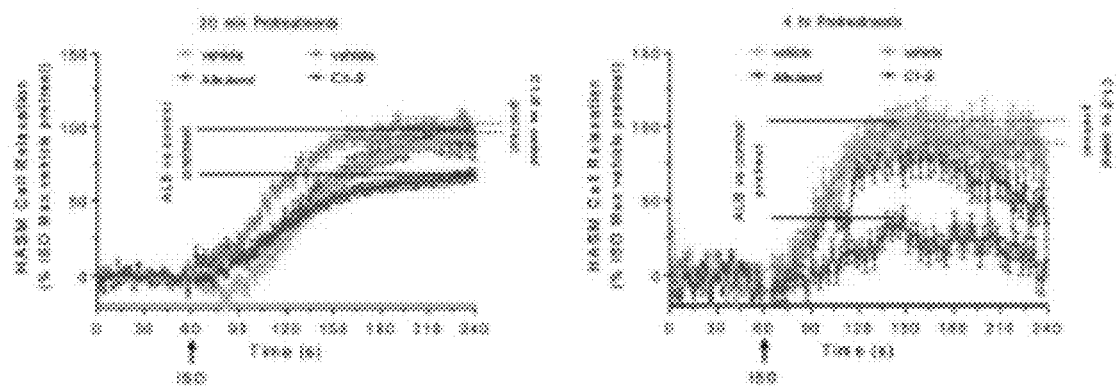
FIG. 6B depicts ALB, but not C1-S, preexposure evokes desensitization of $β_2AR$-mediated HASM cell relaxation. HASM were pretreated with vehicle (control) or 1.0 mM ALB or 100 mM C1-S for 30 min or 4 hours, washed, and then the $β_2AR$ relaxation response to 10 mM ISO determined.
Figure 6C:
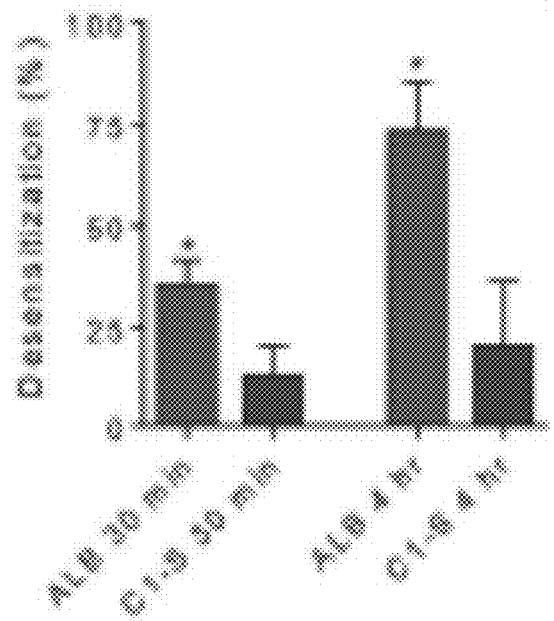
FIG. 6C depicts maximal desensitization to ALB and C1-S. ALB caused desensitization of the relaxation response with 30 min and 4-hour pretreatment, while C1-S evoked no statistically significant desensitization with either pretreatment time. * P<0.01, ** P<0.001 vs vehicle pretreatment responses to ISO. Results are from measurements from 103-387 cells per condition.
Figure 7:
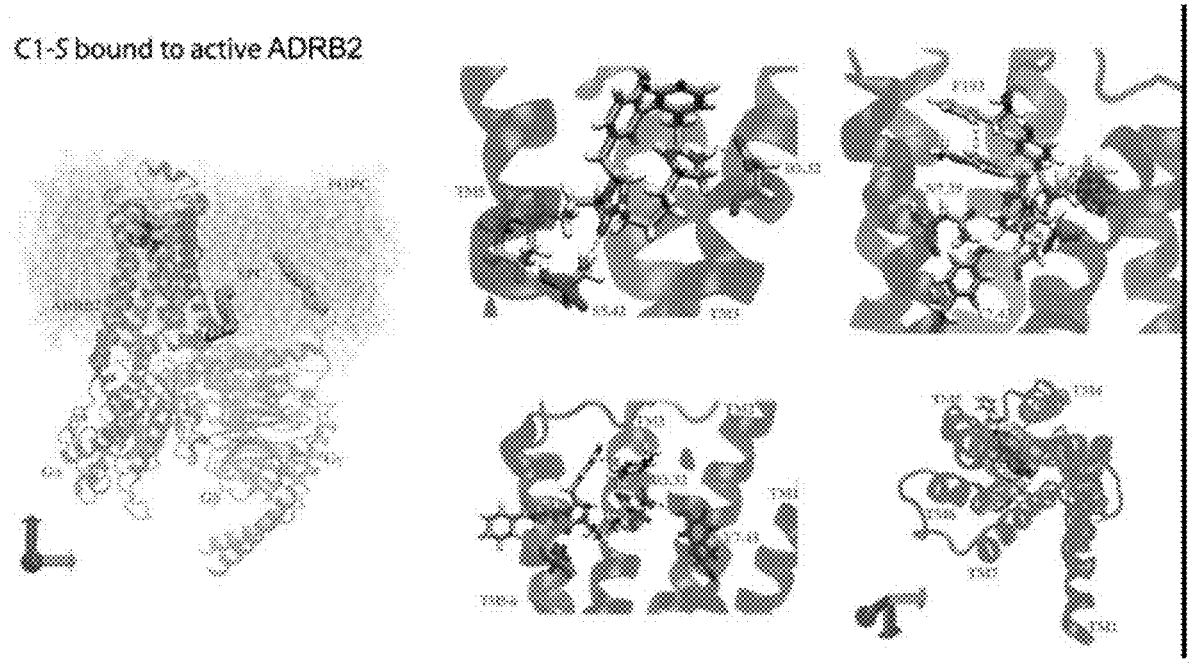
FIG. 7 depicts the predicted binding site for C1-S binding to $β_2AR$ coupled to Gs in explicit membrane and water. The minimized activated $β_2AR$ (blue)-C1-S (yellow)-Gs protein [Gαs (red), Gβ (grey), and Gγ (orange)] in the POPC membrane (light blue). Also depicted are selected interactions of C1-S with activated $β_2AR$: the imidazole forms a SB to $Asp113^{3.32}$ and a HB to $Asn312^{7.39}$, the urea forms a HB to $Ser203^{5.42}$, and π-π stacking of both aromatic rings of the agonist to each other and to $Phe193^{ECL2}$ is evident, internal receptor interaction of $Asp113^{3.32}$ with $Tyr316^{7.43}$, upper view of the compound in the TM pocket.
Figure 8:
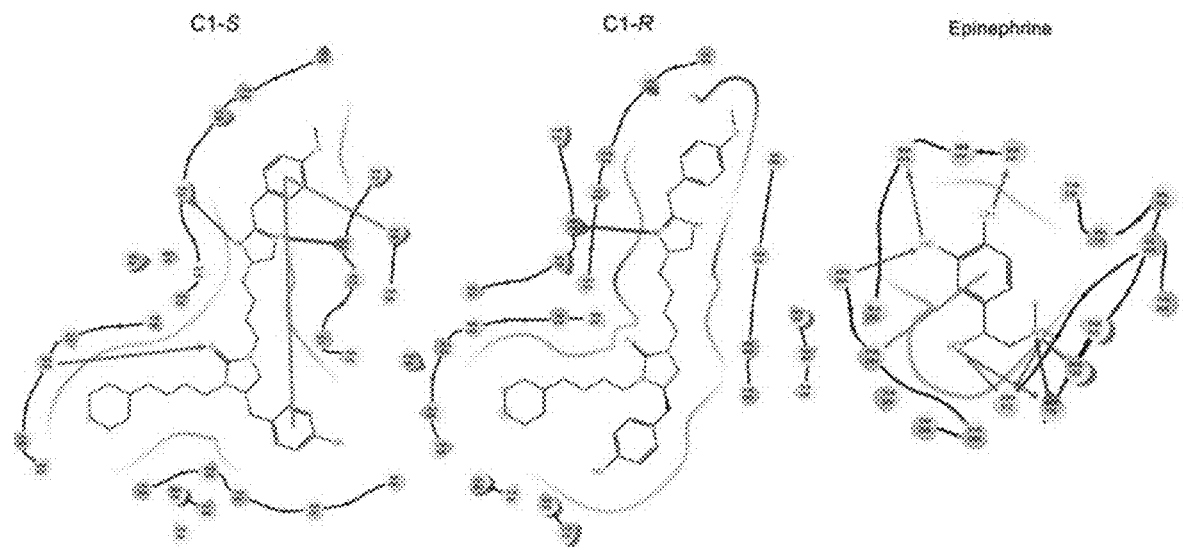
FIG. 8 depicts a comparison of predicted binding site pharmacophores for three ligands bound to active-state $β_2AR$. C1-S binding sites include: HB (pink arrows) to $Ser203^{5.42}$ and $Asn312^{7.39}$; salt bridge (SB, purple line) to $Asp113^{3.32}$; π-π stacking at $Phe193^{ECL2}$ with an internal aromatic bond (green line). The binding site of C1-R is characterized primarily by the SB to $Asp113^{3.32}$; Epinephrine binding sites include: HB to $Ser203^{5.42}$, $Ser207^{5.46}$, $Asn293^{6.55}$, $Asn312^{7.39}$ and $Asp113^{3.32}$, SB to $Asp113^{3.32}$, cation-π interaction with $Phe193^{ECL2}$, p-stacking with $Phe290^{6.52}$, and an intrareceptor HB between $Ser204^{5.43}$ and $Asn293^{6.55}$.
Figure 9:
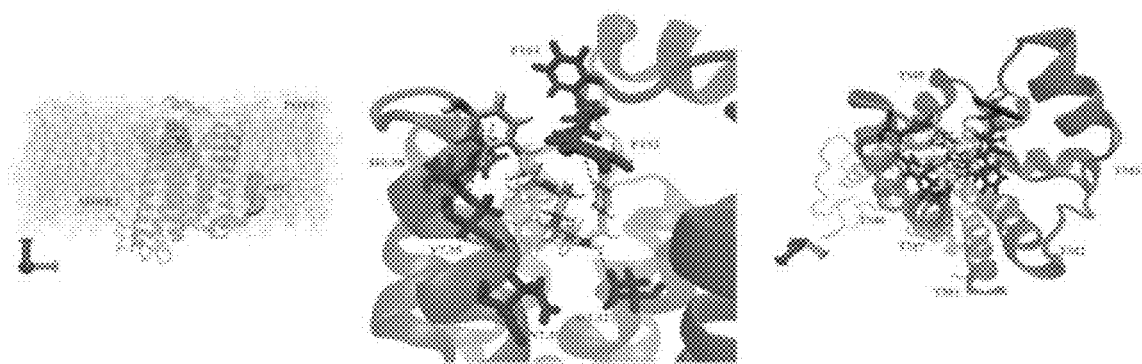
FIG. 9 depicts interactions of C1-R with inactive $β_2AR$ (apo-$β_2AR$). The minimized inactive $β_2AR$ (blue)-C1-S (yellow) complex in the POPC membrane (light blue). The binding pocket of C1-R in the inactive $β_2AR$ includes $Asp113^{3.32}$, $His296^{6.58}$, and aromatic interactions with $Phe193^{ECL2}$, placed in the TM3-4-5-6-7 region.
Figure 10:
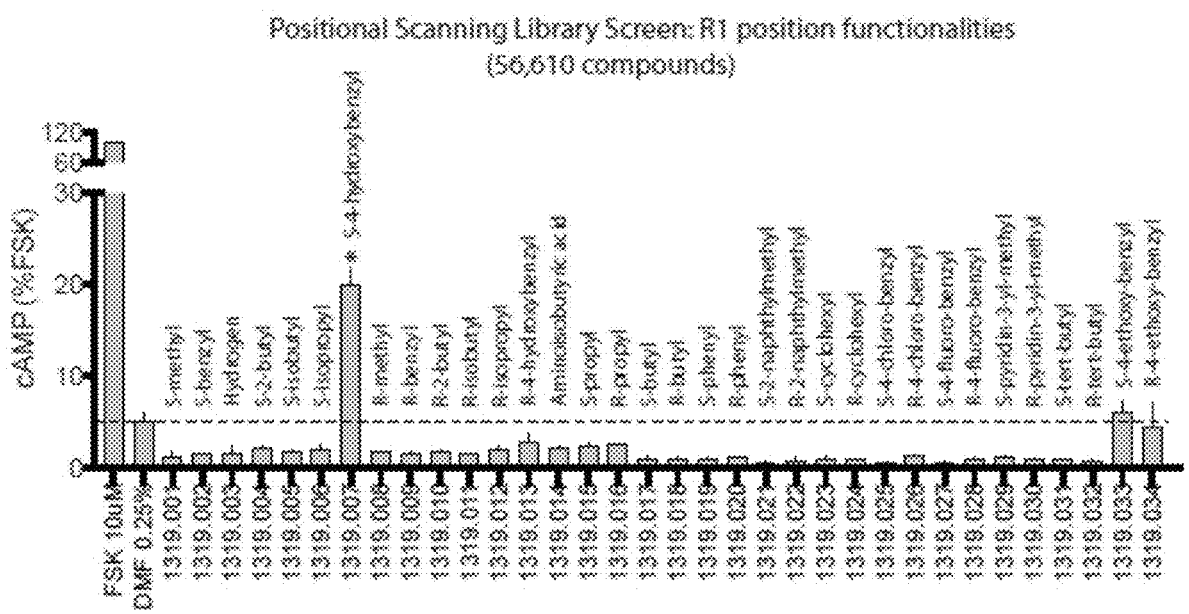
FIG. 10 depicts the results from cAMP screening of CHW-$β_2$ cells with a 56,610 compound positional scanning library with all potential R1 moieties in the library. Each well contained 1,665 compounds. Only well 1319.007 showed a significant increase over baseline.

MTC was used to measure dynamic changes in the cytoskeletal stiffness as a surrogate for agonist-induced single-cell relaxation. Ferrimagnetic microbeads (4.5 mm in diameter) coated with synthetic peptides containing Arg-Gly-Asp (RGD) were ligated to cell surface integrin receptors that form focal adhesions and tightly linked to the underlying cytoskeleton network (see FIG. 6A). Beads were magnetized horizontally to cell plating, and then twisted in a vertically aligned magnetic field that varied sinusoidally in time. Forced bead motions were detected optically with a spatial resolution of ~5 nm, and their changes monitored, in real time, in response to b-agonist (HASM cell relaxation). For desensitization studies (see large arrows in FIG. 6A), cells were treated with vehicle (control), 1.0 μM albuterol, or 100 μM of the agonist C1-S for 30 min or 4-hrs at 37° C. in a 5% $CO_2$, 95% air incubator. Cells were then rapidly washed three times at room temperature with phosphate buffered saline, fresh media applied, and a baseline established for 60 sec. The response to 10 μM isoproterenol (final concentration) added to the media was then determined every 1.3 sec. Isoproterenol relaxes HASM, so the signal decreases. For clarity, the data were transformed so that the Y-axis is labeled "relaxation", which has positive values. The greatest relaxation change from baseline observed at any point over the time course was utilized to quantify the maximal HASM response to isoproterenol.

cAMP values from the screens were compared by ANOVA followed by post-hoc t-tests with Tukey's correction for multiple comparisons. The basal (Rmin), maximal (Rmax), the concentration resulting in half maximal response ($EC_{50}$), the Hill coefficient, and the $R^2$ of the fit for each concentration-response curve was obtained by iterative 4 parameter least squares logistic regression fitting to a sigmoid curve using Prism (GraphPad). The Emax (Rmax–Rmin) and $EC_{50}$ values were compared by t-tests using the same software. For the PLA, ECA and the Gs-activation studies, data were fit to a 3-parameter logistic function with Hill coefficient set at 1.0. The bias factor was calculated from the Gas-activation and ECA data using the logistic equiactive method. Other data as indicated were compared by t-tests with Tukey's correction for multiple comparisons. P values of <0.05 were considered statistically significant. Data from multiple experiments are shown as mean±SE.

Further Embodiments

Embodiment 1: A compound having the formula:

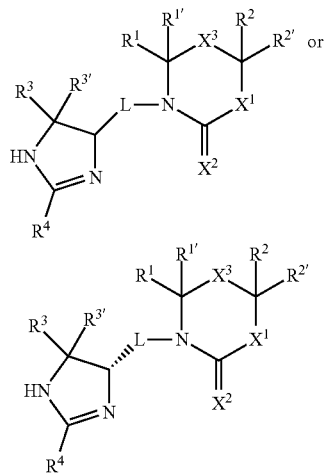

or a pharmaceutically acceptable salt thereof, wherein:
$R^1$ is selected from $Z^1$—$R^{1a}$, $Z^1$—$OR^{1a}$, $Z^1$—$N(R^{1a})_2$, $Z^1$—C(O)Ria; $Z^1$—C(O)$OR^{1a}$, $Z^1$—$OCOR^{1a}$; $Z^1$—C(O)N($R^{1a}$)$_2$, F, Cl, Br, I, cyano, and nitro, wherein $R^{1a}$ is in each case independently selected from hydrogen, $C_{1-8}$alkyl, $C_{2-8}$alkenyl, $C_{2-8}$alkynyl, aryl, $C_{1-8}$heteroaryl, $C_{3-8}$cycloalkyl, or $C_{1-8}$heterocyclyl; and $Z^1$ is null or —(CH$_2$)$_{n1}$— wherein n1 is 1-6;

$R^{1'}$ is selected from $Z^{1'}$—$R^{1'}$, $Z^{1'}$—$OR^{1a'}$, $Z^{1'}$—N($R^{1a'}$)$_2$, $Z^{1'}$—C(O)$R^{1a'}$; $Z^{1'}$—C(O)$OR^{1a'}$, $Z^{1'}$—$OCOR^{1a'}$; $Z^{1'}$—C(O)N($R^{1a'}$)$_2$, F, Cl, Br, I, cyano, and nitro, wherein $R^{1a'}$ is in each case independently selected from hydrogen, $C_{1-8}$alkyl, $C_{2-8}$alkenyl, $C_{2-8}$alkynyl, aryl, $C_{1-8}$heteroaryl, $C_{3-8}$cycloalkyl, or $C_{1-8}$heterocyclyl; and $Z^{1'}$ is null or —(CH$_2$)$_{n1'}$— wherein n1' is 1-6;

$R^2$ is selected from $Z^2$—$R^{2a}$, $Z^2$—$OR^{2a}$, $Z^2$—N($R^{2a}$)$_2$, $Z^2$—C(O)$R^{2a}$; $Z^2$—C(O)$OR^{2a}$, $Z^2$—$OCOR^{2a}$; $Z^2$—C(O)N($R^{2a}$)$_2$, F, Cl, Br, I, cyano, and nitro, wherein $R^{2a}$ is in each case independently selected from hydrogen, $C_{1-8}$alkyl, $C_{2-8}$alkenyl, $C_{2-8}$alkynyl, aryl, $C_{1-8}$heteroaryl, $C_{3-8}$cycloalkyl, or $C_{1-8}$heterocyclyl; and $Z^2$ is null or —(CH$_2$)$_{n2}$— wherein n2 is 1-6;

$R^{2'}$ is selected from $Z^{2'}$—$R^{2a'}$, $Z^{2'}$—$OR^{2a'}$, $Z^{2'}$—N($R^{2a'}$)$_2$, $Z^{2'}$—C(O)$R^{2a'}$; $Z^{2'}$—C(O)$OR^{2a'}$, $Z^{2'}$—$OCOR^{2a'}$; $Z^{2'}$—C(O)N($R^{2a'}$)$_2$, F, Cl, Br, I, cyano, and nitro, wherein $R^{2a'}$ is in each case independently selected from hydrogen, $C_{1-8}$alkyl, $C_{2-8}$alkenyl, $C_{2-8}$alkynyl, aryl, $C_{1-8}$heteroaryl, $C_{3-8}$cycloalkyl, or $C_{1-8}$heterocyclyl; and $Z^{2'}$ is null or —(CH$_2$)$_{n2'}$— wherein n2' is 1-6;

$R^3$ is selected from $Z^3$—$R^{3a}$, $Z^3$—$OR^{3a}$, $Z^3$—N($R^{3a}$)$_2$, $Z^3$—C(O)$R^{3a}$; $Z^3$—C(O)$OR^{3a}$, $Z^3$—$OCOR^{3a}$; $Z^3$—C(O)N($R^{3a}$)$_2$, F, Cl, Br, I, cyano, and nitro, wherein $R^{3a}$ is in each case independently selected from hydrogen, $C_{1-8}$alkyl, $C_{2-8}$alkenyl, $C_{2-8}$alkynyl, aryl, $C_{1-8}$heteroaryl, $C_{3-8}$cycloalkyl, or $C_{1-8}$heterocyclyl; and $Z^3$ is null or —(CH$_2$)$_{n3}$— wherein n3 is 1-6;

$R^{3'}$ is selected from $Z^{3'}$—$R^{3a'}$, $Z^{3'}$—$OR^{3a'}$, $Z^{3'}$—N($R^{3a'}$)$_2$, $Z^{3'}$—C(O)$R^{3a'}$; $Z^{3'}$—C(O)$OR^{3a'}$, $Z^{3'}$—$OCOR^{3a'}$; $Z^{3'}$—C(O)N($R^{3a'}$)$_2$, F, Cl, Br, I, cyano, and nitro, wherein $R^{3a'}$ is in each case independently selected from hydrogen, $C_{1-8}$alkyl, $C_{2-8}$alkenyl, $C_{2-8}$alkynyl, aryl, $C_{1-8}$heteroaryl, $C_{3-8}$cycloalkyl, or $C_{1-8}$heterocyclyl; and $Z^{3'}$ is null or —(CH$_2$)$_{n3'}$— wherein n3' is 1-6;

$R^4$ is selected from $Z^4$—$R^{4a}$, $Z^4$—$OR^{4a}$, $Z^4$—N($R^{4a}$)$_2$, $Z^4$—C(O)$R^{4a}$; $Z^4$—C(O)$OR^{4a}$, $Z^4$—$OCOR^{4a}$; $Z^4$—C(O)N($R^{4a}$)$_2$, F, Cl, Br, I, cyano, and nitro, wherein $R^{4a}$ is in each case independently selected from hydrogen, $C_{1-8}$alkyl, $C_{2-8}$alkenyl, $C_{2-8}$alkynyl, aryl, $C_{1-8}$heteroaryl, $C_{3-8}$cycloalkyl, or $C_{1-8}$heterocyclyl; and $Z^4$ is null or —(CH$_2$)$_{n4}$— wherein n4 is 1-6;

$X^1$ is selected from O, $CHR^5$, and $NR^5$, wherein $R^5$ is selected from H, $C_{1-8}$alkyl, $C_{2-8}$alkenyl, $C_{2-8}$alkynyl, $C_{3-10}$cycloalkyl, aryl, heteroaryl, $C_{1-8}$alk-$C_{3-10}$cycloalkyl, $C_{1-8}$alk-aryl, $C_{1-6}$heterocyclyl, $C_{1-8}$alk-heteroaryl, and $C_{1-8}$alk-$C_{1-6}$heterocyclyl;

$X^2$ is selected from S and O;

$X^3$ is selected from null, —$CR^6R^{6'}$—, wherein
$R^6$ is selected from $Z^6$—$R^{6a}$, $Z^6$—$OR^{6a}$, $Z^6$—N($R^{6a}$)$_2$, $Z^6$—C(O)$R^{6a}$; $Z^6$—C(O)$OR^{6a}$, $Z^6$—$OCOR^{6a}$; $Z^6$—C(O)N($R^{6a}$)$_2$, F, Cl, Br, I, cyano, and nitro, wherein $R^{6a}$ is in each case independently selected from hydrogen, $C_{1-8}$alkyl, $C_{2-8}$alkenyl, $C_{2-8}$alkynyl, aryl, $C_{1-8}$heteroaryl, $C_{3-8}$cycloalkyl, or $C_{1-8}$heterocyclyl; and $Z^6$ is null or —(CH$_2$)$_{n6}$— wherein n6 is 1-6;

$R^{6'}$ is selected from $Z^{6'}$—$R^{6'a}$, $Z^{6'}$—$OR^{6'a}$, $Z^{6'}$—N($R^{6'a}$)$_2$, $Z^{6'}$—C(O)$R^{6'a}$; $Z^{6'}$—C(O)$OR^{6'a}$, $Z^{6'}$—$OCOR^{6'a}$, $Z^{6'}$—C(O)N($R^{6'a}$)$_2$, F, Cl, Br, I, cyano, and nitro, wherein $R^{6'a}$ is in each case independently selected from hydrogen, $C_{1-8}$alkyl, $C_{2-8}$alkenyl, $C_{2-8}$alkynyl, aryl, $C_{1-8}$heteroaryl, $C_{3-8}$cycloalkyl, or $C_{1-8}$heterocyclyl; and $Z^{6'}$ is null or —$(CH_2)_{n6'}$— wherein n6' is 1-6;

wherein any two or more of $R^1$, $R^{1'}$, $R^2$, $R^{2'}$, $R^3$, $R^{3'}$, $R^4$, $R^5$, $R^6$, or $R^{6'}$ may together form a ring.

Embodiment 2: The compound of any preceding embodiment, wherein L is —$(CH_2)_{L1}$—, —$(CH_2)_{L2}O(CH_2)_{L2}$—, or —$(CH_2)_{L2}NR^L(CH_2)_{L2}$—, wherein L1 is 1-6 and L2 is in each case independently selected from 0-4; and $R^L$ is H or $C_{1-4}$alkyl.

Embodiment 3: The compound of any preceding embodiment, having the formula:

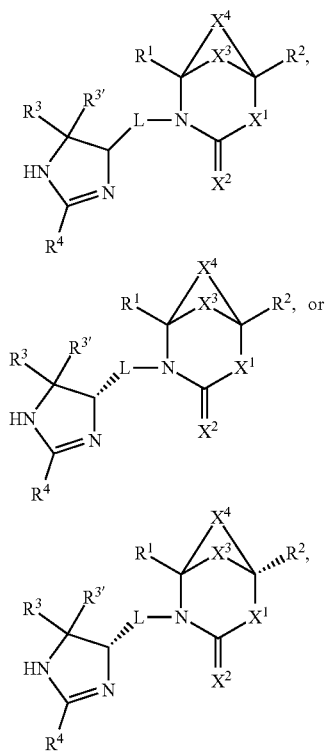

wherein $X^4$ is or —$(CH_2)_{n7}$—, —$(CH_2)_{n8}O(CH_2)_{n8}$—, or —$(CH_2)_{n8}NR^7(CH_2)_{n8}$—, wherein n7' is 1-6 and n8 is independently selected from 0-4; and $R^7$ is selected from $Z^7$—$R^{7a}$, $Z^7$—$OR^{7a}$, $Z^7$—$N(R^{7a})_2$, $Z^7$—$C(O)R^{7a}$; $Z^7$—$C(O)OR^{7a}$, $Z^7$—$OCOR^{7a}$; $Z^7$—$C(O)N(R^{7a})_2$, F, Cl, Br, I, cyano, and nitro, wherein $R^{7a}$ is in each case independently selected from hydrogen, $C_{1-8}$alkyl, $C_{2-8}$alkenyl, $C_{2-8}$alkynyl, aryl, $C_{1-8}$heteroaryl, $C_{3-8}$cycloalkyl, or $C_{1-8}$heterocyclyl; and $Z^7$ is null or —$(CH_2)_{n7}$— wherein n7 is 1-6.

Embodiment 4: The compound of any preceding embodiment, having the formula:

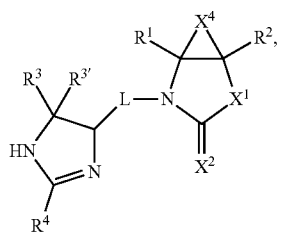

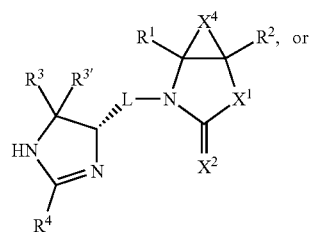

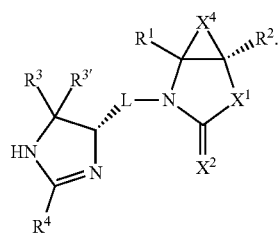

Embodiment 5: The compound of any preceding embodiment, wherein $R^{1'}$ is H.

Embodiment 6: The compound of any preceding embodiment, wherein $R^{2'}$ is H.

Embodiment 7: The compound of any preceding embodiment, having the formula:

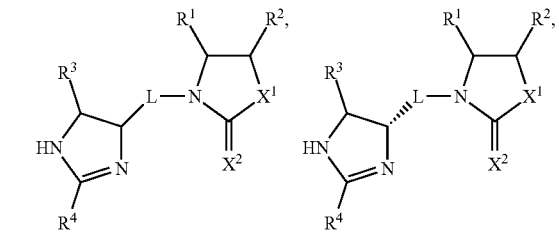

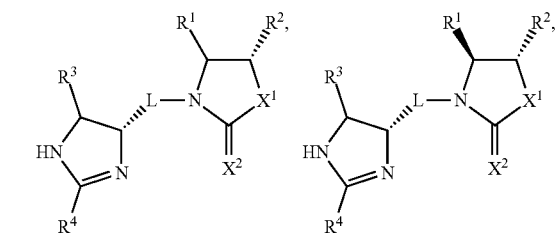

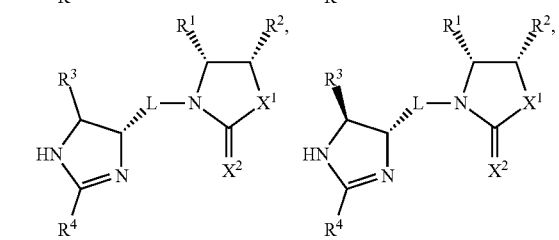

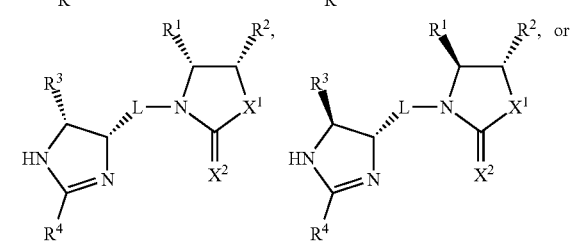

-continued

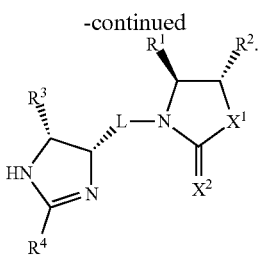

Embodiment 8: The compound of any preceding embodiment, wherein $R^3$ and $R^{3'}$ are each H.

Embodiment 9: The compound of any preceding embodiment, having the formula:

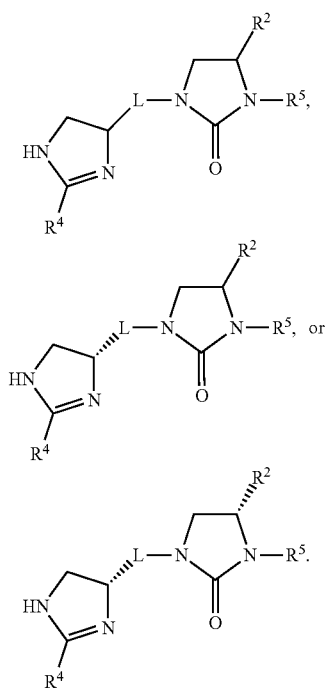

Embodiment 10: The compound of any preceding embodiment, wherein $R^2$ is $Z^2$—$R^{2a}$; and $Z^2$ is null, methylene, or ethylene, and $R^{2a}$ is aryl or heteroaryl.

Embodiment 11: The compound of any preceding embodiment, wherein $R^{2a}$ is an aryl group having the formula:

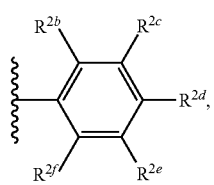

wherein $R^{2b}$ is selected from H, $C_{1-6}$alkyl, OH, $OC_{1-6}$alkyl, $NH_2$, $NHC_{1-6}$alkyl, $N(C_{1-6}alkyl)_2$;
wherein $R^{2c}$ is selected from H, $C_{1-6}$alkyl, OH, $OC_{1-6}$alkyl, $NH_2$, $NHC_{1-6}$alkyl, $N(C_{1-6}alkyl)_2$;
wherein $R^{2d}$ is selected from H, $C_{1-6}$alkyl, OH, $OC_{1-6}$alkyl, $NH_2$, $NHC_{1-6}$alkyl, $N(C_{1-6}alkyl)_2$;
wherein $R^{2e}$ is selected from H, $C_{1-6}$alkyl, OH, $OC_{1-6}$alkyl, $NH_2$, $NHC_{1-6}$alkyl, $N(C_{1-6}alkyl)_2$;
wherein $R^{2d}$ is selected from H, $C_{1-6}$alkyl, OH, $OC_{1-6}$alkyl, $NH_2$, $NHC_{1-6}$alkyl, $N(C_{1-6}alkyl)_2$; and
wherein any two or more of $R^{2b}$, $R^{2c}$, $R^{2d}$, $R^{2e}$, and $R^{2f}$ may together form a ring.

Embodiment 12: The compound of any preceding embodiment, wherein $R^{2b}$ and $R^{2f}$ are each H.

Embodiment 13: The compound of any preceding embodiment, wherein $R^{2c}$, $R^{2d}$, and $R^{2e}$ are each independently selected from H, OH, and $OC_{1-6}$alkyl; wherein any two or more of $R^{2c}$, $R^{2d}$, and $R^{2e}$ may together form a ring.

Embodiment 14: The compound of any preceding embodiment, wherein $R^{2c}$ and $R^{2e}$ are each H.

Embodiment 15: The compound of any preceding embodiment, where $R^{2d}$ is OH.

Embodiment 16: The compound of any preceding embodiment, wherein $X^1$ is $NR^5$.

Embodiment 17: The compound of any preceding embodiment, wherein $R^5$ is $C_{1-8}$alk-$C_{3-10}$cycloalkyl, $C_{1-8}$alk-aryl, $C_{1-6}$heterocyclyl, $C_{1-8}$alk-heteroaryl, or $C_{1-8}$alk-$C_{1-6}$heterocyclyl.

Embodiment 18: The compound of any preceding embodiment, wherein $R^5$ is $C_{1-8}$alk-$C_{3-10}$cycloalkyl or $C_{1-8}$alk-aryl.

Embodiment 19: The compound of any preceding embodiment, wherein $R^5$ is $C_{4-8}$alk-$C_{3-10}$cycloalkyl or $C_{4-8}$alk-aryl.

Embodiment 20: The compound of any preceding embodiment, wherein $R^5$ is $C_{4-8}$alk-cyclohexyl, $C_{4-8}$alk-cyclopentyl, $C_{4-8}$alk-cycloheptyl, $C_{4-8}$alk-cyclooctyl, $C_{4-8}$alk-norbornanyl, octyl $C_{4-8}$alk-bicyclo[2.2.2]octyl, or $C_{4-8}$alk-adamantyl.

Embodiment 21: The compound of any preceding embodiment, wherein $R^4$ is $Z^4$—$R^{4a}$; and $Z^4$ is null, methylene, or ethylene, and $R^{4a}$ is aryl or heteroaryl.

Embodiment 22: The compound of any preceding embodiment, wherein $R^{4a}$ is an aryl group having the formula:

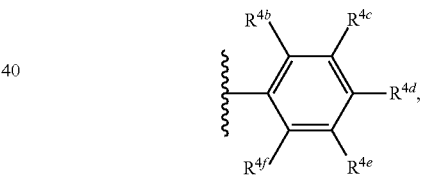

wherein $R^{4b}$ is selected from H, $C_{1-6}$alkyl, OH, $OC_{1-6}$alkyl, $NH_2$, $NHC_{1-6}$alkyl, $N(C_{1-6}alkyl)_2$;
wherein $R^{4c}$ is selected from H, $C_{1-6}$alkyl, OH, $OC_{1-6}$alkyl, $NH_2$, $NHC_{1-6}$alkyl, $N(C_{1-6}alkyl)_2$;
wherein $R^{4d}$ is selected from H, $C_{1-6}$alkyl, OH, $OC_{1-6}$alkyl, $NH_2$, $NHC_{1-6}$alkyl, $N(C_{1-6}alkyl)_2$;
wherein $R^{4e}$ is selected from H, $C_{1-6}$alkyl, OH, $OC_{1-6}$alkyl, $NH_2$, $NHC_{1-6}$alkyl, $N(C_{1-6}alkyl)_2$;
wherein $R^{4d}$ is selected from H, $C_{1-6}$alkyl, OH, $OC_{1-6}$alkyl, $NH_2$, $NHC_{1-6}$alkyl, $N(C_{1-6}alkyl)_2$; and
wherein any two or more of $R^{4b}$, $R^{4c}$, $R^{4d}$, $R^{4e}$, and $R^{4f}$ may together form a ring.

Embodiment 23: The compound of any preceding embodiment, wherein $R^{4b}$ and $R^{4f}$ are each H.

Embodiment 24: The compound of any preceding embodiment, wherein $R^{4c}$, $R^{4d}$, and $R^{4e}$ are each independently selected from H, OH, and $OC_{1-6}$alkyl; wherein any two or more of $R^{4c}$, $R^{4d}$, and $R^{4e}$ may together form a ring.

Embodiment 25: The compound of any preceding embodiment, wherein $R^{4c}$ and $R^{4e}$ are each H.

Embodiment 26: The compound of any preceding embodiment, where $R^{4d}$ is OH, $OCH_3$, or $OCH_2CH_3$.

Embodiment 27: A method for treating an obstructive lung disease in a patient in need thereof, comprising administering to the patient a compound according to any preceding embodiment.
Embodiment 28: The method according to embodiment 27, wherein the obstructive lung disease is asthma, chronic obstructive pulmonary disease, emphysema, bronchitis, cystic fibrosis, bronchiectasis, bronchiolitis, or allergic bronchopulmonary aspergillosis.
Embodiment 29: The method according to any preceding method embodiment, wherein the compound is administered by nasal or buccal inhalation.
Embodiment 30: A pharmaceutical composition, comprising at least one compound according to any of embodiments 1-26, and a pharmaceutically acceptable excipient.
Embodiment 31: The pharmaceutical composition according to embodiment 30, comprising a fluorocarbon solvent.
Embodiment 32: The pharmaceutical composition according to embodiment 30, comprising a powdered matrix material.

The compositions and methods of the appended claims are not limited in scope by the specific compositions and methods described herein, which are intended as illustrations of a few aspects of the claims and any compositions and methods that are functionally equivalent are intended to fall within the scope of the claims. Various modifications of the compositions and methods in addition to those shown and described herein are intended to fall within the scope of the appended claims. Further, while only certain representative compositions and method steps disclosed herein are specifically described, other combinations of the compositions and method steps also are intended to fall within the scope of the appended claims, even if not specifically recited. Thus, a combination of steps, elements, components, or constituents may be explicitly mentioned herein or less, however, other combinations of steps, elements, components, and constituents are included, even though not explicitly stated. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed. Other than in the examples, or where otherwise noted, all numbers expressing quantities of ingredients, reaction conditions, and so forth used in the specification and claims are to be understood at the very least, and not as an attempt to limit the application of the doctrine of equivalents to the scope of the claims, to be construed in light of the number of significant digits and ordinary rounding approaches

What is claimed is:

1. A compound having the formula:

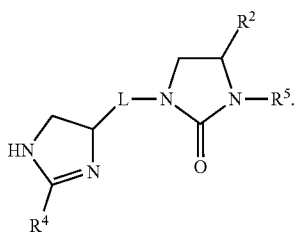

or a pharmaceutically acceptable salt thereof, wherein:

$R^2$ is $Z^2$—$R^{2a}$; wherein $Z^2$ is null, methylene, or ethylene, and $R^{2a}$ is aryl or heteroaryl;
$R^4$ is $Z^4$—$R^{4a}$; wherein $Z^4$ is null, methylene, or ethylene, and $R^{4a}$ is aryl or heteroaryl;
$R^5$ is $C_{1-8}$alk-$C_{3-10}$cycloalkyl, $C_{1-8}$alk-aryl, $C_{1-8}$heterocyclyl, $C_{1-8}$alk-heteroaryl, or $C_{1-8}$alk-$C_{1-6}$heterocyclyl;
L is —$(CH_2)_{L1}$—, —$(CH_2)_{L2}O(CH_2)_{L2}$—, or —$(CH_2)_{L2}NR^L(CH_2)_{L2}$—, wherein L1 is 1-6 and L2 is in each case independently selected from 0-4; and $R^L$ is H or $C_{1-4}$alkyl.

2. The compound of claim 1, wherein L is —$(CH_2)_{L1}$— and L1 is 1-6.

3. The compound of claim 1, wherein $R^{2a}$ is an aryl group having the formula:

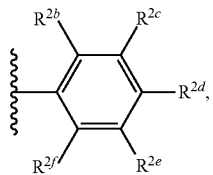

wherein
$R^{2b}$ is selected from H, $C_{1-6}$alkyl, OH, $C_{1-6}$alkyl-OH, $OC_{1-6}$alkyl, $NH_2$, $NHC_{1-6}$alkyl, or $N(C_{1-6}$alkyl$)_2$;
$R^{2c}$ is selected from H, $C_{1-6}$alkyl, OH, $C_{1-6}$alkyl-OH, $OC_{1-6}$alkyl, $NH_2$, $NHC_{1-6}$alkyl, or $N(C_{1-6}$alkyl$)_2$;
$R^{2d}$ is selected from H, $C_{1-6}$alkyl, OH, $C_{1-6}$alkyl-OH, $OC_{1-6}$alkyl, $NH_2$, $NHC_{1-6}$alkyl, or $N(C_{1-6}$alkyl$)_2$;
$R^{2e}$ is selected from H, $C_{1-6}$alkyl, OH, $C_{1-6}$alkyl-OH, $OC_{1-6}$alkyl, $NH_2$, $NHC_{1-6}$alkyl, or $N(C_{1-6}$alkyl$)_2$;
$R^{2f}$ is selected from H, $C_{1-6}$alkyl, OH, $C_{1-6}$alkyl-OH, $OC_{1-6}$alkyl, $NH_2$, $NHC_{1-6}$alkyl, or $N(C_{1-6}$alkyl$)_2$; and wherein any two or more of $R^{2b}$, $R^{2c}$, $R^{2d}$, $R^{2e}$, and $R^{2f}$ may together form a ring.

4. The compound of claim 1, wherein $R^5$ is $C_{4-8}$alk-$C_{3-10}$cycloalkyl or $C_{4-8}$alk-aryl.

5. The compound of claim 4, wherein $R^5$ is $C_{4-8}$alk-cyclohexyl, $C_{4-8}$alk-cyclopentyl, $C_{4-8}$alk-cycloheptyl, $C_{4-8}$alk-cyclooctyl, $C_{4-8}$alk-norbornanyl, $C_{4-8}$alk-bicyclo[2.2.2]octyl, or $C_{4-8}$alk-adamantyl.

6. The compound of claim 1, wherein $R^{4a}$ is an aryl group having the formula

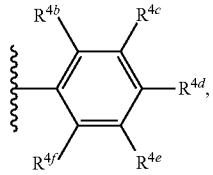

$R^{4b}$ is selected from H, $C_{1-6}$alkyl, OH, $C_{1-6}$alkyl-OH, $OC_{1-6}$alkyl, $NH_2$, $NHC_{1-6}$alkyl, or $N(C_{1-6}$alkyl$)_2$;
$R^{4c}$ is selected from H, $C_{1-6}$alkyl, OH, $C_{1-6}$alkyl-OH, $OC_{1-6}$alkyl, $NH_2$, $NHC_{1-6}$alkyl, or $N(C_{1-6}$alkyl$)_2$;
$R^{4d}$ is selected from H, $C_{1-6}$alkyl, OH, $C_{1-6}$alkyl-OH, $OC_{1-6}$alkyl, $NH_2$, $NHC_{1-6}$alkyl, or $N(C_{1-6}$alkyl$)_2$;
$R^{4e}$ is selected from H, $C_{1-6}$alkyl, OH, $C_{1-6}$alkyl-OH, $OC_{1-6}$alkyl, $NH_2$, $NHC_{1-6}$alkyl, or $N(C_{1-6}$alkyl$)_2$;
$R^{4f}$ is selected from H, $C_{1-6}$alkyl, OH, $C_{1-6}$alkyl-OH, $OC_{1-6}$alkyl, $NH_2$, $NHC_{1-6}$alkyl, or $N(C_{1-6}$alkyl$)_2$; and wherein any two or more of $R^{4b}$, $R^{4c}$, $R^{4d}$, $R^{4e}$, and $R^{4f}$ may together form a ring.

7. The compound of claim 1, wherein the compound has the structure:

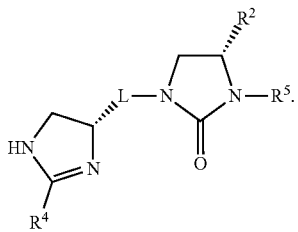

8. The compound of claim 1, wherein the compound has the structure:

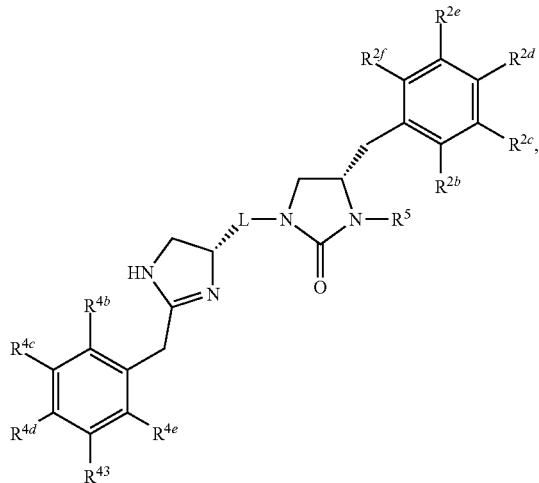

wherein
$R^{2b}$ is selected from H, $C_{1-6}$alkyl, OH, $C_{1-6}$alkyl-OH, $OC_{1-6}$alkyl, $NH_2$, $NHC_{1-6}$alkyl, or $N(C_{1-6}alkyl)_2$;
$R^{2c}$ is selected from H, $C_{1-6}$alkyl, OH, $C_{1-6}$alkyl-OH, $OC_{1-6}$alkyl, $NH_2$, $NHC_{1-6}$alkyl, or $N(C_{1-6}alkyl)_2$;
$R^{2d}$ is selected from H, $C_{1-6}$alkyl, OH, $C_{1-6}$alkyl-OH, $OC_{1-6}$alkyl, $NH_2$, $NHC_{1-6}$alkyl, or $N(C_{1-6}alkyl)_2$;
$R^{2e}$ is selected from H, $C_{1-6}$alkyl, OH, $C_{1-6}$alkyl-OH, $OC_{1-6}$alkyl, $NH_2$, $NHC_{1-6}$alkyl, or $N(C_{1-6}alkyl)_2$;
$R^{2f}$ is selected from H, $C_{1-6}$alkyl, OH, $C_{1-6}$alkyl-OH, $OC_{1-6}$alkyl, $NH_2$, $NHC_{1-6}$alkyl, or $N(C_{1-6}alkyl)_2$;
wherein any two or more of $R^{2b}$, $R^{2c}$, $R^{2d}$, $R^{2e}$, and $R^{2f}$ may together form a ring;
$R^{4b}$ is selected from H, $C_{1-6}$alkyl, OH, $C_{1-6}$alkyl-OH, $OC_{1-6}$alkyl, $NH_2$, $NHC_{1-6}$alkyl, or $N(C_{1-6}alkyl)_2$;
$R^{4c}$ is selected from H, $C_{1-6}$alkyl, OH, $C_{1-6}$alkyl-OH, $OC_{1-6}$alkyl, $NH_2$, $NHC_{1-6}$alkyl, or $N(C_{1-6}alkyl)_2$;
$R^{4d}$ is selected from H, $C_{1-6}$alkyl, OH, $C_{1-6}$alkyl-OH, $OC_{1-6}$alkyl, $NH_2$, $NHC_{1-6}$alkyl, or $N(C_{1-6}alkyl)_2$;
$R^{4e}$ is selected from H, $C_{1-6}$alkyl, OH, $C_{1-6}$alkyl-OH, $OC_{1-6}$alkyl, $NH_2$, $NHC_{1-6}$alkyl, or $N(C_{1-6}alkyl)_2$;
$R^{4f}$ is selected from H, $C_{1-6}$alkyl, OH, $C_{1-6}$alkyl-OH, $OC_{1-6}$alkyl, $NH_2$, $NHC_{1-6}$alkyl, or $N(C_{1-6}alkyl)_2$; and
wherein any two or more of $R^{4b}$, $R^{4c}$, $R^{4d}$, $R^{4e}$, and $R^{4f}$ may together form a ring.

9. The compound of claim 8, wherein both $R^{2b}$ and $R^{2f}$ are H, and $R^{2c}$, $R^{2d}$, and $R^{2e}$ are each independently selected from H, OH, $C_{1-6}$alkyl-OH, and $OC_{1-6}$alkyl; wherein any two or more of $R^{2c}$, $R^{2d}$, and $R^{2e}$ may together form a ring.

10. The compound of claim 8, wherein both $R^{4b}$ and $R^{4f}$ are H, and $R^{4c}$, $R^{4d}$, and $R^{4e}$ are each independently selected from H, OH, and $OC_{1-6}$alkyl; wherein any two or more of $R^{4c}$, $R^{4d}$, and $R^{4e}$ may together form a ring.

11. The compound of claim 8, wherein the compound has the structure:

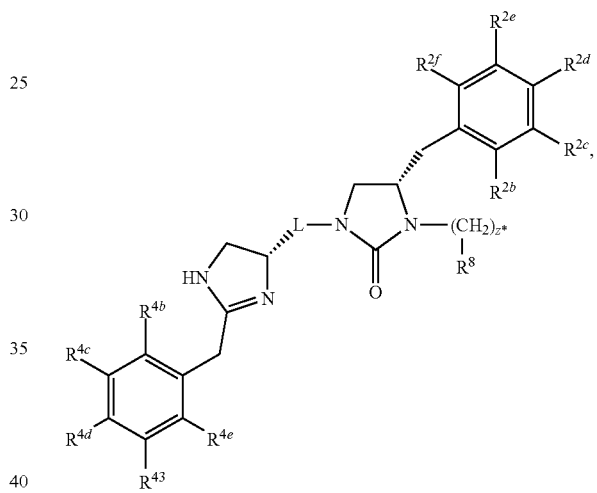

wherein z* is 1, 2, 3, 4, 5, or 6, and $R^8$ is $C_{3-10}$cycloalkyl.

12. The compound of claim 11, wherein $R^8$ is cyclohexyl, cycloheptyl, cyclooctyl, norbornanyl, bicyclo[2.2.2]octyl, or adamantyl.

13. A pharmaceutical composition, comprising a compound of claim 1, and a pharmaceutically acceptable excipient.

14. A method for treating an obstructive lung disease in a patient in need thereof, comprising administering to the patient a compound of claim 1.

* * * * *